(12) United States Patent
Tuscano et al.

(10) Patent No.: US 9,480,725 B2
(45) Date of Patent: Nov. 1, 2016

(54) FERMENTED WHEAT GERM PROTEINS (FWGP) FOR THE TREATMENT OF CANCER

(75) Inventors: Joseph Tuscano, Folsom, CA (US); Derick Lau, Roseville, CA (US); Robert O'Donnell, Sacramento, CA (US); Yunpeng Ma, Chengdu (CN)

(73) Assignee: The Regents of the University of California, Oakland, CA (US)

( * ) Notice: Subject to any disclaimer, the term of this patent is extended or adjusted under 35 U.S.C. 154(b) by 166 days.

(21) Appl. No.: 13/320,898

(22) PCT Filed: May 20, 2010

(86) PCT No.: PCT/US2010/035656
§ 371 (c)(1),
(2), (4) Date: Jan. 20, 2012

(87) PCT Pub. No.: WO2010/135580
PCT Pub. Date: Nov. 25, 2010

(65) Prior Publication Data
US 2012/0121612 A1    May 17, 2012

Related U.S. Application Data

(60) Provisional application No. 61/180,089, filed on May 20, 2009, provisional application No. 61/180,096, filed on May 20, 2009.

(51) Int. Cl.
*A61K 36/899* (2006.01)
*A61K 38/16* (2006.01)

(52) U.S. Cl.
CPC ........... *A61K 36/899* (2013.01); *A61K 38/168* (2013.01)

(58) Field of Classification Search
None
See application file for complete search history.

(56) References Cited

FOREIGN PATENT DOCUMENTS

WO    WO2004/014406    2/2004

OTHER PUBLICATIONS

Boros et al., Ann. N.Y. Acad. Sci., 2005, 1051, 529-542.*
International Search Report for PCT/US2010/035656 mailed on Jan. 25, 2011.
Boros et al., Fermented Wheat Germ Extract (Avemar) in the Treatment of Cancer and Autoimmune Diseases. Ann NY Acad, 2005, vol. 1051, pp. 529-542, see abstract, pp. 533, 534.
Smith et al., Nucleotide Sequences of cDNA Clones Encoding Wheat Germ Agglutinin Isolectins A and D, Plant Molecular Biology, 1989, vol. 13, pp. 601-603. See abstract.
Van Campenhout et al., The Applicability of Consensus PCR Primers Across Species and Genera: The Use of Wheat EM Sequences to Develop Markers for Orthologues in Rye, Theor. Appl. Genet., 2000, vol. 100, pp. 328-336. See whole element.
Greene et al. (1980) "Inhibition of Human Lymphocyte Proliferation by the Nonmitogenic Lectin Wheat Germ Agglutinin" *The Journal of Immunology* 124(6): 2979-2987.
Huang, et al., Nature (Lond) (2000) 407:390-395.

* cited by examiner

*Primary Examiner* — James H Alstrum Acevedo
*Assistant Examiner* — Roy Teller
(74) *Attorney, Agent, or Firm* — Weaver Austin Villeneuve & Sampson LLP

(57) ABSTRACT

The present invention provides compositions comprising the component of fermented wheat germ extract ("FWGE") active in reducing, inhibiting or preventing the proliferation of cancer cells and/or tumors, and methods of making and using such compositions. The active component from FWGE comprises polypeptides having a molecular weight in the range of about 5-100 kiloDaltons (kD), for example, a molecular weight in the range of about 12-50 kD. Exemplary polypeptides from FWGE determined to be active in reducing, inhibiting or preventing the proliferation of cancer cells and/or tumors are listed in Table 1.

42 Claims, 18 Drawing Sheets

FERMENTED WHEAT GERM PROTEINS (FWGP) FOR THE TREATMENT OF CANCER

CROSS-REFERENCES TO RELATED APPLICATIONS

This application is a U.S. National Phase filing under 35 U.S.C. §371 of International Application No. PCT/US2010/035656, filed on May 20, 2010, which claims the benefit of U.S. Provisional Application No. 61/180,089, filed on May 20, 2009 and U.S. Provisional Application No. 61/180,096, filed on May 20, 2009, each of which are hereby incorporated herein by reference in their entirety for all purposes.

FIELD OF THE INVENTION

The present invention provides compositions comprising the component of fermented wheat germ extract ("FWGE") active in reducing, inhibiting or preventing the proliferation of cancer cells and/or tumors, and methods for making and using such compositions. The active component from FWGE comprises polypeptides having a molecular weight in the range of about 5-100 kiloDalton (kD), for example, a molecular weight in the range of about 12-50 kD. Exemplary polypeptides from FWGE determined to be active in reducing, inhibiting or preventing the proliferation of cancer cells and/or tumors are listed in Table 1.

BACKGROUND OF THE INVENTION

According to a nationwide government survey released in December 2008, approximately 38% of U.S. adults and approximately 12% of children use some form of complementary and alternative medicines (CAM) (information can be found on the World Wide Web at nccam.nih.gov/news/camstats/2007/camsurvey_fsl.htm). This study revealed that the use of many forms of CAM significantly increased in prevalence between 2002 and 2007. Although not specifically studied, the incidence of CAM use in oncology patients is likely even higher due to a desperate attempt of many cancer patients to find therapies that are believed to be more effective and less toxic than conventional medicines. This same time period has also seen large numbers of articles in the lay press extolling the benefits of these therapies thereby increasing awareness of them in the general population. Together, increased opportunity and increased awareness may explain much of the observed increase in adult use of CAM.

While the use of these therapies has increased, scientific research provided only limited evidence of clinical efficacy. For instance, the National Library of Medicine journal database, PubMed, identified 40 systematic reviews published between 2002 and 2007. Of these, only 10 (25%) of the systematic reviews found sufficient evidence to conclude that a given CAM therapy was effective for a given condition. While many believe that some of these therapies have significant therapeutic potential, there needs to be better, more rigorous scientific studies to back up the purported claims before they can be recommended for use (information can be found on the World Wide Web at nccam.nih.gov/news/camstats/2007/camsurvey_fsl.htm).

Growth inhibition of Ehrlich ascites tumor can be achieved by treatment of tumor-bearing mice with a mixture of 2,6-dimethoxy-p-benzoquinone-DMBQ and ascorbic acid (Pethig, R. et al., Proc. Natl. Acad. Sci. U.S.A. 80:129 (1983).). This mixture produces long-lived semiquinone and ascorbic free radicals. Vitamin C is present in many plants, while DMBQ is present in wheat germ. It has been shown that quenching of quinone and ascorbic radicals depends on an NADPH-dependent SH group containing enzyme (Pethig, R. et al., Proc. Natl. Acad. Sci. U.S.A. 81:2088 (1984).). The cytotoxicity of the radical mixture was supposed to be associated with the decreased NADP-reducing capacity of tumor cells (Pethig, R. et al., Proc. Natl. Acad. Sci. U.S.A. 82:1439 (1985).). During the fermentation of wheat germ, yeast quinones are released by the glycosidase enzyme of the yeast. It has been hypothesized that the biological activity of these released quinones relates to "immunostimulatory effects". Based on this hypothesis studies by Szent-Györgyi, produced a dried standardized extract of wheat germ fermented by Saccharomyces cereiisiae. The fermentation process had previously been optimized to yield DMBQ in the extract. The dried extract was named MSC (Trade name: AVEMAR) (Pethig, R. et al., Proc. Natl. Acad. Sci. U.S.A. 80:129 (1983); and Zalatnai, et al., Carcinogenesis, 22(10):1649-1652 (2001)). The final product, Avemar pulvis, comprises 63.2% fermented wheat germ, 35.0% maltodextrin, and 1.8% colloidal silicon dioxide. The product has been reported to be standardized to the DMBQ content (Tomoskozi-Farkas and Daood, 2004; Fajka-Boja, Int J. Oncol. 2002 (3):563-70). Flavors and sweeteners, including fructose, natural orange flavor and sodium chloride have been added to Avemar pulvis and the product sold under trade name, Ave', in the United States (American Biosciences, Inc. Blauvelt, N.Y.).

Preliminary in vitro studies with MSC have demonstrated induction of apoptosis and necrosis in pancreatic carcinoma cells, T lymphocytic tumor cell lines, and leukemia cells in vitro (Boros L G et al., Pancreas 23:141-147 (2001); Comin-Anduix B et al., J Biol Chem 277:46408-46414 (2002); and Fajka-Boja R et al., Int J Oncol 20:563-570 (2002)). In T lymphoid tumor cells, apoptosis was selectively induced via tyrosine phosphorylation and calcium influx (Fajka-Boja R et al., Int J Oncol 20:563-570 (2002).). In addition, MSC was shown to have a selective inhibitory effect on glycolysis and pentose cycle enzymes, and to cause the down-regulation of major histocompatibility complex class I proteins in tumor cells (Boros L G et al., Pancreas 23:141-147 (2001); Comin-Anduix B et al., J Biol Chem 277:46408-46414 (2002); and Fajka-Boja R et al., Int J Oncol 20:563-570 (2002)). Avemar treatment for 24 hrs caused necrosis in 28% and apoptosis in 22% of the cells. Avemar inhibited the cell-cycle progression of HT-29 colon cancer cells in the G1 phase of the cell cycle. In addition, Avemar inhibited the activity of the key enzyme of de novo DNA synthesis, ribonucleotide reductase. In addition, Avemar inhibited the activity of cyclooxygenase-1 and -2. Although no chemical constituents are yet isolated and tested experimentally, it has been hypothesized that benzoquinones, wheat germ agglutinin (WGA), fiber, lipids and phytic acid in wheat bran play a role in exerting anti-carcinogenic effects. In a recent report utilizing intracellular carbon flow studies with a $^{13}$C-labeled isotope of glucose and biological mass spectrometry (GC/MS), it was demonstrated that fermented wheat germ inhibits nucleic acid ribose synthesis in a dose dependent fashion primarily through the non-oxidative steps of the pentose cycle while increasing direct glucose carbon oxidation and acetyl-CoA utilization toward fatty acid synthesis in pancreatic adenocarcinoma cells (information can be found on the World Wide Web at nccam.nih.gov/news/camstats/2007/camsurvey_fsl.htm). These metabolic changes indicate that FWGE exerts its anti-proliferative action through altering metabolic enzyme activities which primarily control glucose carbon flow toward nucleic acid synthesis.

BRIEF SUMMARY OF THE INVENTION

In one aspect, the invention provides methods of preventing, reducing and/or inhibiting the growth or proliferation of a cancer cell or tumor. In some embodiments, the methods comprise contacting the cancer cell with an isolated fraction from fermented wheat germ extract ("FWGE") comprising low molecular weight polypeptides with a molecular weight in the range of about 5-100 kiloDaltons (kD), wherein the isolated fraction is substantially isolated or purified from (i.e., substantially separated from) non-proteinaceous (i.e., not polypeptides or peptides) components of FWGE.

In a further aspect, the invention provides methods of preventing, reducing and/or inhibiting the growth or proliferation of a cancer cell or tumor in a subject in need thereof. In some embodiments, the methods comprise administering to the subject an effective amount of an isolated fraction from fermented wheat germ extract ("FWGE") comprising low molecular weight polypeptides with a molecular weight in the range of about 5-100 kiloDaltons (kD), wherein the isolated fraction is substantially isolated or purified from non-proteinaceous components of FWGE.

In a related aspect, the invention provides methods of preventing, reducing and/or inhibiting the growth or proliferation of a cancer cell or tumor. In some embodiments, the method comprises contacting the cancer cell with one or more of the polypeptides listed in Table 1.

In a further aspect, the invention provides methods of preventing, reducing and/or inhibiting the growth or proliferation of a cancer cell or tumor in a subject in need thereof. In some embodiments, the methods comprise administering to the subject an effective amount of one or more of the polypeptides listed in Table 1.

With respect to the embodiments of the methods, in some embodiments, the isolated fraction from fermented wheat germ extract ("FWGE") comprises low molecular weight polypeptides with a molecular weight in the range of about 5-100 kD, for example, a molecular weight in the range of about 10-90 kD, 10-80 kD, 10-70 kD, 10-60 kD, 12-50 kD, 5-60 kD, 5-50 kD, 5-40 kD, 5-30 kD or 5-20 kD. In some embodiments, the isolated fraction is substantially purified or isolated from peptides or polypeptides having larger or smaller molecular weights, as described herein.

In some embodiments, the cancer cell is in vivo. In some embodiments, the cancer cell is in vitro.

In some embodiments, the cancer is selected from the group consisting of lymphoma, lung cancer, breast cancer, colon cancer, and hepatic cancer. In some embodiments, the cancer is a lymphoma. In some embodiments, the cancer is a lung cancer. Further cancers subject to treatment and prevention are described herein.

In some embodiments, the isolated fraction from fermented wheat germ extract comprises one or more polypeptides listed in Table 1, or fragments thereof. In some embodiments, the isolated FWGP comprises a mixture of two or more polypeptides from Table 1, e.g., 2, 3, 4, 5, 6, 7, 8, 9, 10, 11, 12, 13, 14, 15, 16, 17, 18, 19, 20 or more polypeptides listed in Table 1, or fragments thereof. In other embodiments, the isolated FWGP comprises a mixture of all the polypeptides listed in Table 1, or fragments thereof.

In some embodiments, the isolated FWGP or one or more peptides or polypeptides of Table 1 is co-administered with one or more antibodies that specifically bind to a tumor associated antigen. Exemplary antibodies are described herein. The antibody can be a human or humanized antibody.

In some embodiments, the subject or patient is a human.

In some embodiments, the isolated FWGP or one or more peptides or polypeptides of Table 1 are administered systemically (e.g., orally, intravenously) or locally (e.g., topically). Administration can be by a physician to the subject, or self-administration by the patient.

In a further aspect, the invention further provides compositions comprising an isolated fraction from fermented wheat germ extract ("FWGE") comprising low molecular weight polypeptides with a molecular weight in the range of about 5-100 kD, wherein the isolated fraction is substantially isolated or purified from non-proteinaceous components of FWGE, and a pharmaceutically acceptable excipient.

With respect to the embodiments of the compositions, in some embodiments, the isolated fraction from fermented wheat germ extract ("FWGE") comprises low molecular weight polypeptides with a molecular weight in the range of about 5-100 kD, for example, a molecular weight in the range of about 10-90 kD, 10-80 kD, 10-70 kD, 10-60 kD, 12-50 kD, 5-60 kD, 5-50 kD, 5-40 kD, 5-30 kD or 5-20 kD. In some embodiments, the isolated fraction is substantially purified or isolated from peptides or polypeptides having larger or smaller molecular weights, as described herein.

In some embodiments, the isolated fraction from fermented wheat germ extract comprises one or more polypeptides listed in Table 1, or fragments thereof. In some embodiments, the isolated FWGP comprises a mixture of two or more polypeptides from Table 1, e.g., 2, 3, 4, 5, 6, 7, 8, 9, 10, 11, 12, 13, 14, 15, 16, 17, 18, 19, 20 or more polypeptides listed in Table 1, or fragments thereof. In other embodiments, the isolated FWGP comprises a mixture of all the polypeptides listed in Table 1, or fragments thereof.

In some embodiments, the compositions further comprise one or more antibodies that specifically bind to a tumor associated antigen.

In some embodiments, the compositions are formulated for oral administration.

In another aspect, the invention further provides kits comprising an isolated fraction from fermented wheat germ extract ("FWGE") comprising low molecular weight polypeptides with a molecular weight in the range of about 5-100 kiloDaltons (kD), wherein the isolated fraction is substantially isolated or purified from non-proteinaceous components of FWGE. The isolated FWGP or the one or more peptides or polypeptides of Table 1 may further be formulated a pharmaceutically acceptable excipient.

With respect to the embodiments of the kits, in some embodiments, the isolated fraction from fermented wheat germ extract ("FWGE") comprises low molecular weight polypeptides with a molecular weight in the range of about 5-100 kD, for example, a molecular weight in the range of about 10-90 kD, 10-80 kD, 10-70 kD, 10-60 kD, 12-50 kD, 5-60 kD, 5-50 kD, 5-40 kD, 5-30 kD or 5-20 kD. In some embodiments, the isolated fraction is substantially purified or isolated from peptides or polypeptides having larger or smaller molecular weights, as described herein.

In some embodiments, the isolated fraction from fermented wheat germ extract comprises one or more polypeptides listed in Table 1, or fragments thereof. In some embodiments, the isolated FWGP comprises a mixture of two or more polypeptides from Table 1, e.g., 2, 3, 4, 5, 6, 7, 8, 9, 10, 11, 12, 13, 14, 15, 16, 17, 18, 19, 20 or more polypeptides listed in Table 1, or fragments thereof. In other embodiments, the isolated FWGP comprises a mixture of all the polypeptides listed in Table 1, or fragments thereof.

In some embodiments, the kits further comprise one or more antibodies that specifically bind to a tumor associated antigen.

The components of the kits can be formulated as mixtures or separately.

Further embodiments of the invention are described herein.

DEFINITIONS

The terms "fermented wheat germ extract" and FWGE and variants thereof refer to an extract prepared from a mixture of fresh wheat germ that has been blended and fermented and insoluble portions removed.

The terms "fermented wheat germ extract polypeptides" or "FWGP" and variants thereof refer to an isolated proteinaceous fraction from FWGE (i.e., polypeptides and peptides) active in inhibiting, reducing and/or preventing the growth of cancer cells. The FWGP described herein is substantially isolated and/or purified from (i.e., separated from) the non-proteinaceous fraction of FWGE and generally comprises polypeptides and peptides with molecular weights ranging from 5-100 kD. Polypeptides in the FWGP are listed in Table 1.

The term "isolated," and variants thereof when applied to a protein (e.g., polypeptides and/or polypeptides of FWGP), denotes that the protein is essentially free of other cellular components with which it is associated in the natural state. It is preferably in a homogeneous state. It can be in either a dry or aqueous solution. Purity and homogeneity are typically determined using known techniques, such as polyacrylamide gel electrophoresis or high performance liquid chromatography. A protein that is the predominant species present in a preparation is substantially purified.

The term "isolated fraction" and variants of variants thereof when applied to a FWGE fraction denotes that the preparation is essentially free of other cellular components with which it is associated in the natural state. It is preferably in a homogeneous state. It can be in either a dry or aqueous solution. Purity and homogeneity are typically determined using known techniques, such as polyacrylamide gel electrophoresis or high performance liquid chromatography. Proteins are the predominant species present in an isolated fraction preparation. The preparation can contain a specific size protein fraction, for example, polypeptides or peptides having a molecular weights in the range of about 5-100 kD, for example, a molecular weight in the range of about 10-90 kD, 10-80 kD, 10-70 kD, 10-60 kD, 12-50 kD, 5-60 kD, 5-50 kD, 5-40 kD, 5-30 kD or 5-20 kD.

The term "purified" denotes that a protein (e.g., polypeptides and/or peptides of FWGP) gives rise to essentially one band in an electrophoretic gel. Particularly, it means that the nucleic acid or protein is at least 80%, 85% or 90% pure, more preferably at least 95% pure, and most preferably at least 99% pure.

The terms "systemic administration" and "systemically administered" refer to a method of administering the FWGP or one or more of the polypeptides of Table 1 to a mammal so that the polypeptide or polypeptide composition is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration, with the proviso that, as used herein, systemic administration does not include direct administration to the brain region by means other than via the circulatory system, such as intrathecal injection and intracranial administration.

The term "co-administer" and "co-administering" and variants thereof refer to the simultaneous presence of two or more active agents in the blood of an individual. The active agents that are co-administered can be concurrently or sequentially delivered. As used herein, the co-administered active agents can be two or more polypeptides or peptides in the FWGP or two or more polypeptides or peptides from Table 1. Also, the polypeptides or peptides in the FWGP or from Table 1 can be co-administered with another active agent efficacious in treating or preventing cancer (e.g., an antibody against a tumor associated antigen or a chemotherapeutic agent).

The terms "consisting essentially of" and variants thereof refer to the genera or species of polypeptides included in a method or composition, as well as any excipients inactive for the intended purpose of the methods or compositions. In some embodiments, the phrase "consisting essentially of" expressly excludes the inclusion of insoluble wheat germ portions, for example, the wheat kernel, bran, and endosperm. Generally, compositions comprising the FWGP or one or more of the polypeptides of Table 1 are substantially isolated or purified from non-proteinaceous components of wheat germ, e.g., separated from sugars, lipids and nucleic acids. In some embodiments, the compositions comprising the FWGP or one or more of the polypeptides of Table 1 are substantially isolated or purified from wheat germ polypeptides with a molecular weight that is greater than about 100 kD or less than about 5 kD, for example, greater than about 60 kD or less than about 10 kD, for example, greater than about 50 kD or less than about 12 kD.

The term "neutraceutical" refers to a food or food product that provides health and medical benefits, including the prevention and treatment of disease.

The terms "treating" and "treatment" and variants thereof refer to delaying the onset of, retarding or reversing the progress of, alleviating or preventing either the disease or condition to which the term applies, or one or more symptoms of such disease or condition. Treating and treatment encompass both therapeutic and prophylactic treatment regimens.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to administration of an FWGP or the one or more polypeptides of Table 1. In some embodiments, the growth, progression or spread of a tumor or cancer is inhibited, reduced or decreased by at least about 1-fold, 2-fold, 3-fold, 4-fold, or more in comparison to the tumor burden prior to administration of the FWGP or the one or more polypeptides of Table 1.

The terms "subject," "patient," or "individual" interchangeably refer to any mammal, for example, humans and non-human primates, domestic mammals (e.g., canine, feline), agricultural mammals (e.g., bovine, equine, ovine, porcine) and laboratory mammals (e.g., mouse, rat, rabbit, hamster).

The terms "identical" or percent "identity," and variants thereof in the context of two or more polypeptide sequences, refer to two or more sequences or subsequences that are the same. Sequences are "substantially identical" if they have a specified percentage of amino acid residues or nucleotides that are the same (i.e., at least 60% identity, optionally at least 65%, 70%, 75%, 80%, 85%, 90%, 95%, 96%, 97%, 98%, or 99% identity over a specified region (or the whole reference sequence when not specified)), when compared and aligned for maximum correspondence over a comparison window, or designated region as measured using one of the following sequence comparison algorithms or by manual alignment and visual inspection. The present invention provides polypeptides substantially identical to the polypeptides listed in Table 1. Optionally, the identity exists over a region that is at least about 50 amino acids in length, or more preferably over a region that is 100 to 500 or 1000 or more amino acids in length, or over the full-length of the sequence.

The terms "similarity," or "percent similarity," and variants thereof in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 96%, 97%, 98% or 99% similar over a specified region), when compared and aligned for maximum correspondence over a comparison window, or designated region as measured using one of the following sequence comparison algorithms or by manual alignment and visual inspection. Sequences having less than 100% similarity but that have at least one of the specified percentages are said to be "substantially similar." Optionally, this identity exists over a region that is at least about 50 amino acids in length, or more preferably over a region that is at least about 100 to 500 or 1000 or more amino acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. *APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul *Proc. Natl. Acad. Sci.* (U.S.A.) 87:2264-2268 (1990), or by manual alignment and visual inspection (see, e.g., Ausubel et al., *Current Protocols in Molecular Biology* (1995 supplement)).

Examples of an algorithm that is suitable for determining percent sequence identity and sequence similarity include the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Standard BLAST algorithm parameters have an expected threshold of 10 (according to the stochastic model of Karlin and Altschul (*PNAS*, 87:2264-2268 (1990)); a word size of 28; reward and penalty of 1/−2 (a ratio of 0.5, or 1/−2, is used for sequences that are 95% conserved); and a linear GAP cost.

An "antibody" refers to a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD)

and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used in this application, an "antibody" encompasses all variations of antibody and fragments thereof that possess a particular binding specifically, e.g., for tumor associated antigens. Thus, within the scope of this concept are full length antibodies, chimeric antibodies, humanized antibodies, human antibodies, singly domain antibodies or nanobodies, single chain antibodies (ScFv), Fab, Fab', and multimeric versions of these fragments (e.g., F(ab')$_2$) with the same binding specificity.

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under designated immunoassay conditions, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for the preferential targeting of a pharmacological agent to the cancer cell. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal.

DETAILED DESCRIPTION

1. Introduction

Figure 1:
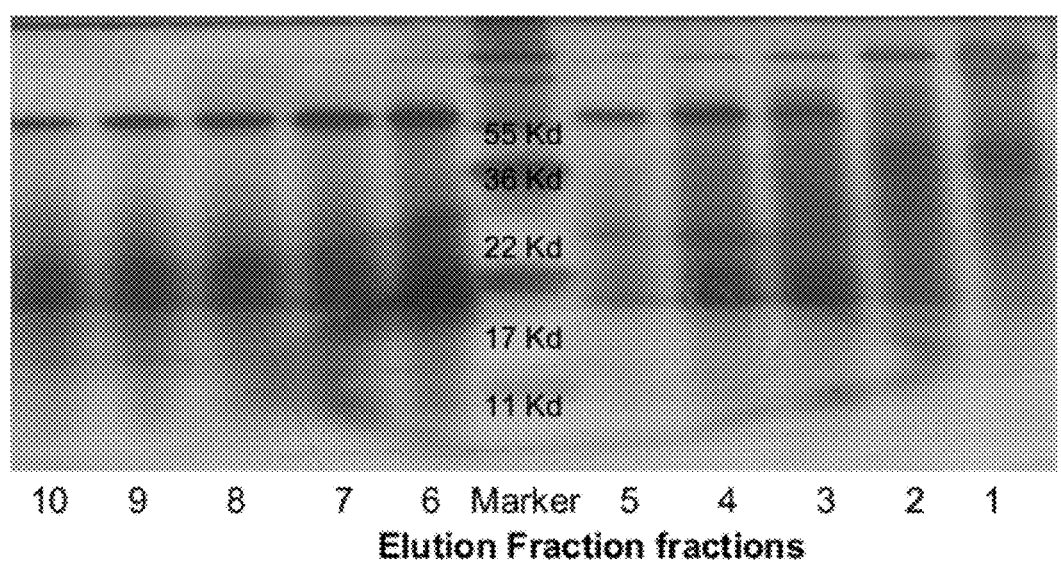
FIG. 1 illustrates polyacrylamide gel electrophoresis of FWGP. Visualization via silver stain.

The present invention is based, in part, on the discovery of the component(s) in fermented wheat germ extract FWGE that is active in reducing, inhibiting or preventing the growth or proliferation cancer cells. The active component(s) of FWGE is proteinaceous and has a molecular weight in the range of about 5-100 kD. Exemplary polypeptides isolated from FWGE with anticancer properties are listed in Table 1.

2. Fermented Wheat Germ Extract Polypeptides Subject to Administration

The fermented wheat germ polypeptides (FWGP) isolated from fermented wheat germ extract (FWGE) contain a variety of polypeptides that find use in the reduction, inhibition and/or prevention of cancer cell proliferation and/or tumor growth. The active fraction of FWGE, the FWGP, comprises polypeptides and peptides substantially isolated or purified from (i.e., separated from) non-proteinaceous components of FWGE, e.g., substantially purified or isolated from sugars, lipids, nucleic acids and insoluble components of FWGE. The active polypeptides in FWGP includes but is not limited to those listed in Table 1 below.

The polypeptides in the FWGP typically have molecular weights in the range of about 5 kD to about 100 kD. In some embodiments, the polypeptides in the FWGP have molecular weights in the range of about 10-90 kD, 10-80 kD, 10-70 kD, 10-60 kD, 12-50 kD, 5-60 kD, 5-50 kD, 5-40 kD, 5-30 kD or 5-20 kD.

In some embodiments, the FWGP is substantially isolated or purified from peptides or polypeptides with molecular weights that are larger or smaller than the stated range of molecular weight. For example, in some embodiments, the FWGP is substantially isolated or purified from peptides or polypeptides that are larger than 100 kD and smaller than 5 kD, for example, peptides or polypeptides that are larger than 90 kD and smaller than 10 kD, for example, peptides or polypeptides that are larger than 80 kD and smaller than 10 kD, for example, peptides or polypeptides that are larger than 70 kD and smaller than 10 kD, for example, peptides or polypeptides that are larger than 60 kD and smaller than 10 kD, for example, peptides or polypeptides that are larger than 50 kD and smaller than 12 kD, for example, peptides or polypeptides that are larger than 60 kD and smaller than 5 kD, for example, peptides or polypeptides that are larger than 50 kD and smaller than 5 kD, for example, peptides or polypeptides that are larger than 40 kD and smaller than 5 kD, for example, peptides or polypeptides that are larger than 30 kD and smaller than 5 kD, for example, peptides or polypeptides that are larger than 20 kD and smaller than 5 kD.

TABLE 1

ANTICANCER POLYPEPTIDES

| Polypeptide | GenBank Nucleic Acid No. | GenBank Amino Acid No. |
|---|---|---|
| early-methionine-labelled polypeptide | CD907884.1 (GI:32682208) | |
| early-methionine-labelled polypeptide (wheat mRNA for Em protein) | Y00123.1 (GI:21732) | CAA68322.1 (GI:21733) |
| early-methionine-labelled polypeptide [rye; *Secale cereale*] | AJ011954.1 (GI:7594659) | CAB88093.1 (GI:7594660) |
| aspartic proteinase (WAP1) | AB219968.1 (GI:73912433) | BAE20413.1 (GI:73912433) |
| aspartic proteinase (WAP2) | AB219969.1 (GI:73912434) | BAE20414.1 (GI:73912435) |
| late embryogenesis abundant protein | X56882.1 (GI:21636) | CAA40204.1 (GI:21637) |
| late embryogenesis abundant protein | BJ299677.1 (GI:23154477) | |
| late embryogenesis abundant protein (Wrab18) | AB297679.1 (GI:157073743) | BAF79927.1 (GI:157073744) |
| *Triticum aestivum* Wrab17 gene for group3 late embryogenesis abundant protein, complete cds. | AB297678.1 (GI:157073741) | BAF79926.1 (GI:157073742) |
| late embryogenesis abundant protein | CJ539338.1 (GI:93156536) | |
| late embryogenesis abundant protein | AB297680.1 (GI:157073745) | BAF79928.1 (GI:157073746) |
| group 3 late embryogenesis abundant protein | AB297678.1 (GI:157073741) | BAF79926.1 (GI:157073742) |
| late embryogenesis abundant protein | M72395.1 (GI:170691) | AAA34267.1 (GI:170692) |
| FGAS022985 *Triticum aestivum* FGAS: Library 6 CAP GATE 1 *Triticum aestivum* cDNA, mRNA sequence | CK211149.1 (GI:39617258) dbEST Id: 20799500 EST name: FGAS022985 | |
| thioredoxin h | AJ404845.1 (GI:8980490) | CAB96931.1 (GI:8980491) |
| Em protein H2 | X73227.1 (GI:312518) | CAA51700.1 (GI:312519) |
| translational inhibitor protein (*Triticum aestivum* FGAS: Library 4 Gate 8) | CK162179.1 (GI:38991125) dbEST Id: 20740621 EST name: FGAS014765 | |
| FGAS051302 *Triticum aestivum* FGAS: TaLt7 *Triticum aestivum* cDNA, mRNA sequence | CK167031.1 (GI:39000698) dbEST Id: 20745473 EST name: FGAS051302 | |
| copper zinc-superoxide dismutase | FJ890986.1 (GI:226897528) | ACO90194.1 (GI:226897529) |
| copper zinc-superoxide dismutase | U69632.1 (GI:1572626) | AAB67991.1 (GI:1572627) |

TABLE 1-continued

ANTICANCER POLYPEPTIDES

| Polypeptide | GenBank Nucleic Acid No. | GenBank Amino Acid No. |
| --- | --- | --- |
| *Triticum aestivum* mRNA for 0.19 alpha-amylase inhibitor, partial cds (dimeric alpha-amylase inhibitor) | AB003682.1 (GI:2575815) | BAA20139.1 (GI:2116581) |
| G468.105F06R010929 G468 *Triticum aestivum* cDNA clone G468105F06, mRNA sequence | CD906690.3 (GI:32681019) dbEST Id: 19085274 EST name: G468.105F06R010929 | |
| wsi18 protein induced by water stress | AP003381.3 (GI:19571079) | BAB86507.1 (GI:19571082) |
| reversibly glycosylated polypeptide | Y18626.1 (GI:4158231) | CAA77237.1 (GI:4158232) |
| FGAS014876 *Triticum aestivum* FGAS: Library 4 Gate 8 *Triticum aestivum* cDNA, mRNA sequence | CK162286.1 (GI:38991338) dbEST Id: 20740728 EST name: FGAS014876 | |
| cold shock protein-1 | AB161683.1 (GI:42391857) | BAD08701.1 (GI:42391858) |
| FGAS021443 *Triticum aestivum* FGAS: Library 5 GATE 7 *Triticum aestivum* cDNA, mRNA sequence | CK209668.1 (GI:39572058) dbEST Id: 20798014 EST name: FGAS021443 | |
| Wheat mRNA for subunit CM3 of alpha-amylase tetrameric inhibitor. (hageman factor inhibitor) | X17574.1 (GI:21712) | CAA35597.1 (GI:21713) |
| FGAS030061 *Triticum aestivum* FGAS: Library 6 CAP GATE 1 *Triticum aestivum* cDNA, mRNA sequence | CK218055.1 (GI:39624159) dbEST Id: 20806401 EST name: FGAS030061 | |
| protein disulfide isomerase | U11496.1 (GI:508974) | AAA19660.1 (GI:508975) |
| Wheat (*T. aestivum*) germ agglutinin isolectin D, complete cds | M25537.1 (GI:170669) | AAA34258.1 (GI:170670) |
| Wheat (*T. aestivum*) germ agglutinin isolectin A, complete cds | M25536.1 (GI:170665) | AAA34256.1 (GI:170666) |
| n-acetylneuraminyllactose-wheat germ agglutinin isolectin complexes | | 1WGC_B (GI:230393) |
| FGAS029900 *Triticum aestivum* FGAS: Library 6 CAP GATE 1 *Triticum aestivum* cDNA, mRNA sequence | CK217898.1 (GI:39624002) dbEST Id: 20806244 EST name: FGAS029900 | |
| FGAS021317 *Triticum aestivum* FGAS: Library 5 GATE 7 *Triticum aestivum* cDNA, mRNA sequence (desiccation-related protein pcc13-62) | CK209547.1 (GI:39571937) dbEST Id: 20797893 EST name: FGAS021317 | |
| BRY_901 BRY *Triticum aestivum* cDNA clone P10-1L, mRNA sequence | AW448620.1 (GI:12019155) dbEST Id: 3859369 EST name: BRY_901 | |
| high molecular weight glutenin subunit | AJ314785.1 (GI:14329762) | CAC40687.1 (GI:14329763) |
| FGAS014507 *Triticum aestivum* FGAS: Library 4 Gate 8 *Triticum aestivum* cDNA, mRNA sequence | CK161927.1 (GI:38990615) dbEST Id: 20740369 EST name: FGAS014507 | |
| group 3 late embryogenesis abundant protein | X56882.1 (GI:21636) | CAA40204.1 (GI:21637) |
| group 3 late embryogenesis abundant protein | M72395.1 (GI:170691) | AAA34267.1 (GI:170692) |
| serpin | Y11485.1 (GI:1885349) | CAA72273.1 (GI:1885350) |
| FGAS045291 *Triticum aestivum* FGAS: TaLt6 *Triticum aestivum* cDNA, mRNA sequence | CK170407.1 (GI:39007571) dbEST Id: 20748849 EST name: FGAS045291 | |
| carboxymethylenebutenolidase-like protein (*Oryza sativa* Japonica Group) | AP003350.3 (GI:20521332) | BAB91862.1 (GI:20521349) |
| FGAS075594 *Triticum aestivum* FGAS: Library 2 Gate 3 *Triticum aestivum* cDNA, mRNA sequence | CV781183.1 (GI:55686123) dbEST Id: 26363797 EST name: FGAS075594 | |
| G608.105K18F010906 G608 *Triticum aestivum* cDNA clone G608105K18, mRNA sequence | CD917520.1 (GI:32691844) dbEST Id: 9096099 EST name: G608.105K18F010906 | |
| ABA-inducible protein WRAB1 | AF139915.1 (GI:4929079) | AAD33850.1 (GI:4929080) |
| WHE2989_H12_P23ZS Wheat dormant embryo cDNA library *Triticum aestivum* cDNA clone WHE2989_H12_P23, mRNA sequence | BQ842188.1 (GI:22211597) dbEST Id: 13132303 EST name: WHE2989_H12_P23ZS | |
| *Triticum aestivum* LEA1 protein (LEA1) mRNA, complete cds | AY148490.1 (GI:25989704) | AAN74637.1 (GI:25989705) |
| *Triticum aestivum* LEA2 protein (LEA2) mRNA, complete cds | AY148491.1 (GI:25989708) | AAN74638.1 (GI:25989709) |
| *Triticum aestivum* LEA3 protein (LEA3) mRNA, complete cds | AY148492.1 (GI:25989706) | AAN74639.1 (GI:25989707) |

TABLE 1-continued

ANTICANCER POLYPEPTIDES

| Polypeptide | GenBank Nucleic Acid No. | GenBank Amino Acid No. |
|---|---|---|
| FGAS017876 *Triticum aestivum* FGAS: Library 5 GATE 7 *Triticum aestivum* cDNA, mRNA sequence (secreted protein) | CK206290.1 (GI:39568680) dbEST Id: 20794636 EST name: FGAS017876 | |

The polypeptides in the FWGP or the one or more polypeptides of Table 1 can be native polypeptides or variants of the native polypeptides. For example, the polypeptides in the FWGP or the one or more polypeptides in Table 1 can be truncated versions or fragments of the active polypeptides. For example, the length of the FWGP or the one or more polypeptides of Table 1 can be 95%, 90%, 85%, 80%, 75%, 70%, 65%, 60%, 55%, 50%, or shorter, of the length of the native polypeptide, e.g., as described in Table 1. Furthermore, analogs including allelic, species and induced variants of the polypeptides in the FWGP or the one or more polypeptides of Table 1 find use.

Analogs of the polypeptides in the FWGP or the one or more polypeptides of Table 1 can differ from naturally occurring peptides at up to 30%, e.g., up to 20%, 15%, 10%, or 5% of amino acid positions, or by up to 1, 2, 3, 4, 5, 6, 7, 8, 9 or 10 position changes. For example, in some embodiments, an analog may vary by up to 1, 2, 3, 4, 5 or 6 position changes. Each deletion or substitution of a natural amino acid residue is considered a position change as is the insertion of a residue without substitution. Amino acids substitutions are often conservative. For purposes of classifying amino acids substitutions as conservative or non-conservative, amino acids are grouped as follows: Group I (hydrophobic sidechains): norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class. Non-conservative substitutions constitute exchanging a member of one of these classes for a member of another.

The FWGP, or the one or more polypeptides of Table 1 include polypeptides that are "substantially identical" or exhibit "substantial similarity." The FWGP, or the one or more polypeptides of Table 1 include polypeptides having at least 60% identity, optionally at least 65%, 70%, 75%, 80%, 85%, 90%, 95%, 98%, or 99% identity to the native polypeptides when compared to the native polypeptides and aligned using sequence comparison algorithms or by manual alignment and visual inspection using methods known to those of skill in the art. In some embodiments, the FWGP, or the one or more polypeptides of Table 1 are identical to or have 100% sequence identity to the polypeptides listed in Table 1.

3. Methods of Producing Fermented Wheat Germ Polypeptide

The FGWP, or the one or more polypeptides of Table 1 can be obtained by any methods known by one of skill in the art. Such methods can include recombinant as well as synthetic methods for polypeptide generation. The polypeptides can also be substantially purified from a fermented wheat germ source.

a. Preparing FWGE and Purifying FWGP from Wheat Germ

The fermented wheat germ extract can be prepared using any wheat germ. Extracts for use in the present invention can also be made starting with commercially available plant extract, such as AVEMAR (plant extract, Biropharma, Ltd., Budapest, Hungary). The fermented wheat germ extract is an extract prepared from a mixture of fresh wheat germ that has been blended to flour-quality and mixed with water and Baker's yeast. The mixture is then shaken, centrifuged and the supernatant collected. The supernatant can be used directly or freeze dried and stored for later use. The freeze dried supernatant is powdered wheat germ extract. The extract comprises a mixture of wheat germ proteins, including but not limited to those located in Table 1. FWGE can be purified and fractionated to obtain FWGP fractions containing a subset of wheat germ proteins. Fractions can for example be based on polypeptide size, charge, or any other polypeptide properties known in the art. FWGP can be alternatively be purified and individual polypeptide components isolated to obtain specific polypeptides, e.g., those listed in Table 1.

FGWP extract or one or more of the polypeptides of Table 1 with anticancer activity can be recovered and purified by methods including, but not limited to, size-exclusion chromatography, ammonium sulfate or ethanol precipitation, TCA precipitation, acid or base extraction, column chromatography, affinity chromatography, affinity column chromatography, anion or cation exchange chromatography, phosphocellulose chromatography, hydrophobic interaction chromatography, hydroxylapatite chromatography, lectin chromatography, gel electrophoresis, as well as others known in the art. A variety of purification/protein folding methods are well-known, see, e.g., Deutscher, Methods in Enzymology Vol. 182: Guide to Protein Purification (Academic Press, Inc. N.Y. 1990); and Bollag et al., Protein Methods, 2nd Edition, (Wiley-Liss, N.Y. 1996), and R. Scopes, Protein Purification, Springer-Verlag, N.Y. (1982)). Substantially pure compositions of at least about 80 to 100% homogeneity are preferred, and 98 to 99% or more homogeneity are most preferred for pharmaceutical uses.

In some preferred embodiments, the polypeptides are isolated or purified based on size exclusion separation procedures. Isolated and/or purified fractions containing the active FWGE polypeptides have molecular weights the range of about 5 to 100 kD, for example, about 10-90 kD, 10-80 kD, 10-70 kD, 10-60 kD, 12-50 kD, 5-60 kD, 5-50 kD, 5-40 kD, 5-30 kD or 5-20 kD.

b. Recombinant and Synthetic Methods of Production

Examples of appropriate molecular techniques for generating recombinant polypeptides for use with the methods of the present invention, and instructions sufficient to direct persons of skill in the art can be found in, e.g., Maniatis, et al., *Molecular Cloning: A Laboratory Manual*, Cold Spring Harbor Lab., New York, 1982 and Ausubel, et al. Editor, *Current Protocols in Molecular Biology*, USA, 1984-2008; Berger and Kimmel, Guide to Molecular Cloning Techniques, Methods in Enzymology (Volume 152 Academic Press, Inc., San Diego, Calif. 1987); all of which are incorporated herein by reference in their entirety. Product information from manufacturers of biological reagents and experimental equipment also provide information useful in known biological methods. Such manufacturers include SIGMA (Saint Louis, Mo.), R&D systems (Minneapolis, Minn.), Pharmacia LKB Biotechnology (Piscataway, N.J.), Clontech Laboratories, Inc. (Palo Alto, Calif.), Aldrich Chemical Company (Milwaukee, Wis.), Invitrogen (San Diego, Calif.), Applied Biosystems (Foster City, Calif.), as well as many other commercial sources known to one of skill in the art.

For recombinant methods of polypeptide production, the nucleic acids encoded for the polypeptides of the present invention must first be prepared. The nucleic acid sequences can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In some embodiments, the nucleic acid sequences are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (3RD ED.), Vols. 1-3, Cold Spring Harbor Laboratory (2001)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987-2009). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding the polypeptides of the present invention can be modified to produce polypeptides that are analogous or substantially identical to the polypeptides naturally found in fermented wheat germ extract (FWGE). Modification by site-directed mutagenesis is well known in the art. Nucleic acids encoding the polypeptides of the present invention can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill in the art.

In one embodiment, polypeptides are prepared by inserting the cDNA which encodes the FWGP polypeptides (e.g., of Table 1) into a vector. Once the nucleic acids encoding the polypeptides of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., FWGP polypeptide, e.g., of Table 1) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

Further, polypeptides can be recombinantly produced in cell-free reaction systems. Various cell-free synthesis reaction systems are well-known in the art and can be combined with the recombinant DNA methodologies described above, as well as any others known in the art, in order to produce the peptides of the present invention. See, e.g., Kim, D. M. and Swartz, J. R. *Biotechnol. Bioeng.* 66:180-8 (1999); Kim, D. M. and Swartz, J. R. *Biotechnol. Prog.* 16:385-90 (2000); Kim, D. M. and Swartz, J. R. *Biotechnol. Bioeng.* 74:309-16 (2001); Swartz et al., Methods Mol. Biol. 267:169-82 (2004); Kim, D. M. and Swartz, J. R. *Biotechnol. Bioeng.* 85:122-29 (2004); Jewett, M. C. and Swartz, J. R., *Biotechnol. Bioeng.* 86:19-26 (2004); Yin, G. and Swartz, J. R., *Biotechnol. Bioeng.* 86:188-95 (2004); Jewett, M. C. and Swartz, J. R., *Biotechnol. Bioeng.* 87:465-72 (2004); Voloshin, A. M. and Swartz, J. R., *Biotechnol. Bioeng.* 91:516-21 (2005) Jewett, et al., *Molec. Systems Bio.* 4(220): 1-10 (2008); U.S. Pat. No. 7,312,049; U.S. Pat. No. 7,351, 563; US 2007/0154983; and US 2009/0042244; all of which are incorporated herein by reference in their entirety.

In addition to recombinant methods, the polypeptides of the present invention can also be constructed in whole or in part using synthetic methods, such as for example but not limited to standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Polypeptide can also be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

4. Compositions Comprising Fermented Wheat Germ Extract Polypeptides

The invention provides compositions containing the wheat germ extract polypeptide fraction (e.g., peptides or polypeptides from fermented wheat germ extract with a molecular weight between 5-100 kD) or one or more of the polypeptides listed in Table 1, or fragments thereof. In some embodiments, the compositions comprise a mixture of two or more polypeptides from Table 1, e.g., 2, 3, 4, 5, 6, 7, 8, 9, 10, 11, 12, 13, 14, 15, 16, 17, 18, 19, 20 or more polypeptides listed in Table 1. In other embodiments, the compositions can comprise a mixture of all the polypeptides listed in Table 1, or fragments thereof.

The fermented wheat germ polypeptide fraction or the one or more polypeptides of Table 1, or fragments thereof, are formulated in a pharmaceutically acceptable carrier, and in some instances combined with other active ingredients. The polypeptides and/or peptides find use in pharmaceutical and neutraceutical formulations.

In some embodiments, fermented wheat germ polypeptide fraction or the one or more polypeptides of Table 1, or fragments thereof, are formulated in nutraceutical compositions comprising. A nutraceutical composition serves as a nutritional supplement upon consumption. In other embodiments, a nutraceutical may be bioactive and serve to affect, alter, or regulate a bioactivity of an organism. The nutraceutical may be in the form of a solid or liquid formulation. In some embodiments, a solid formulation includes a capsule or tablet formulation as described herein. In other embodiments, a solid nutraceutical may simply be a dried polypeptide or peptide extract or homogenate. In liquid formulations, the invention includes suspensions, as well as aqueous solutions, of the polypeptides or peptides, extracts, or homogenates.

Generally, the peptides and polypeptides in the FWGP compositions are substantially purified and/or isolated from (i.e., substantially separated from) non-proteinaceous components of fermented wheat germ, for example, substantially isolated and/or purified from lipids, sugars, nucleic acids and insoluble components of wheat germ.

In some embodiments, the peptides and polypeptides in the FWGP compositions is substantially isolated and/or purified from peptides or polypeptides with molecular weights that are larger or smaller than the stated range of molecular weight. For example, in some embodiments, the FWGP is substantially isolated or purified from peptides or polypeptides that are larger than 100 kD and smaller than 5 kD, for example, peptides or polypeptides that are larger than 90 kD and smaller than 10 kD, for example, peptides or polypeptides that are larger than 80 kD and smaller than 10 kD, for example, peptides or polypeptides that are larger than 70 kD and smaller than 10 kD, for example, peptides or polypeptides that are larger than 60 kD and smaller than 10 kD, for example, peptides or polypeptides that are larger than 50 kD and smaller than 12 kD, for example, peptides or polypeptides that are larger than 60 kD and smaller than 5 kD, for example, peptides or polypeptides that are larger than 50 kD and smaller than 5 kD, for example, peptides or polypeptides that are larger than 40 kD and smaller than 5 kD, for example, peptides or polypeptides that are larger than 30 kD and smaller than 5 kD, for example, peptides or polypeptides that are larger than 20 kD and smaller than 5 kD.

In some embodiments, the peptides and polypeptides in the FWGP compositions are formulated in a mixture with one or more therapeutic antibodies. Examples of therapeutic antibodies that can be co-administered with the FWGP or one or more of the polypeptides of Table 1 include but are not limited to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope); IgG antibody (ImClone System); IMC-C225 which is a chimeric anti-EGFR IgG antibody; VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 which is a humanized anti-ICAM3 antibody (ICOS Pharm); IDEC-114 which is a primate anti-CD80 antibody (IDEC Pharm/Mitsubishi); ZEVALIN™ which is a radiolabelled murine anti-CD20 antibody (IDEC/Schering AG); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); SMART anti-CD3 which is a humanized anti-CD3 IgG (Protein Design Lab); 5G1.1 which is a humanized anti-complement factor 5 (CS) antibody (Alexion Pharm); D2E7 which is a humanized anti-TNF-α antibody (CATIBASF); CDP870 which is a humanized anti-TNF-α Fab fragment (Celltech); IDEC-151 which is a primatized anti-CD4 IgG1 antibody (IDEC Pharm/SmithKline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4,7 antibody (LeukoSite/Genentech); OrthoClone OKT4A which is a humanized anti-CD4 IgG antibody (Ortho Biotech); ANTOVA™ which is a humanized anti-CD40L IgG antibody (Biogen); ANTEGREN™ which is a humanized anti-VLA-4 IgG antibody (Elan); and CAT-152 which is a human anti-TGF-$β_2$ antibody (Cambridge Ab Tech).

Generally, therapeutic antibodies that specifically bind to a tumor-associated antigen ("TAA") find use in mixtures with the FWGP or one or more polypeptides of Table 1. Examples of known TAAs include without limitation, melanoma associated antigens (MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGβ) subunit expressed by many different tumors, including but not limited to myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B cell lymphoma can generate tumor-specific immunity (attributed to idiotype-specific humoral immune response). Moreover, antigens of human T cell leukemia virus type 1 have been shown to induce specific CTL responses and antitumor immunity against the virus-induced human adult T cell leukemia (ATL). See, e.g., Haupt, et al., *Experimental Biology and Medicine* (2002) 227:227-237; Ohashi, et al., *Journal of Virology* (2000) 74(20):9610-9616. Other TAAs are known and find use for co-formulation with the FWGP or one or more of the polypeptides of Table 1.

a. Pharmaceutical Formulations

The can be prepared as a variety of pharmaceutical formulations for administration to a patient, including liquid and solid form preparations.

The polypeptides and pharmaceutical compositions of the present invention are useful for parenteral, topical, oral, or local administration, including by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the polypeptides and pharmaceutical compositions of this invention, when administered orally, must be protected from digestion. This is typically accomplished either by complexing the polypeptide with a composition to render it resistant to acidic and enzymatic hydrolysis or by packaging the protein in an appropriately resistant carrier such as a liposome. Means of protecting proteins from digestion are well known in the art.

The polypeptides and pharmaceutical compositions of the present invention are particularly useful for parenteral administration, such as intravenous administration or administration into a body cavity or lumen of an organ. The compositions for administration will commonly comprise a solution of the polypeptide comprising the polypeptide dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of polypeptide in these formulations can vary widely, and will be selected primarily based on fluid volumes, viscosities, body weight and the like in accordance with the particular mode of administration selected and the patient's needs.

Liquid form pharmaceutical preparations can include solutions, suspensions, and emulsions, for example, water or water/propylene glycol solutions. Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Also contemplated are solid form pharmaceutical formulations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical formulation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such active material for use in humans and animals, as disclosed in detail in this specification, these being features of the present invention.

In one embodiment of the present invention, a pharmaceutical formulation is administered to a patient at a therapeutically effective dose to prevent, treat, or control a disease or malignant condition, such as cancer. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of the disease or malignant condition. An amount adequate to accomplish this is defined as "therapeutically effective dose."

5. Conditions Subject to Prevention and Treatment

The FWGP or one or more of the polypeptides of Table 1 find use in the treatment of cancer. The polypeptides can be administered to a patient to effect the inhibition, reduction, retraction or prevention of proliferation or growth of a tumor or a cancer cell. In the context of effecting treatment, the patient has a cancer or a tumor burden, and administration of the polypeptide fraction or one or more of the polypeptides can reverse, delay or inhibit progression of the disease. In the context of effecting prevention, the patient may be in remission, or may have undergone the removal of a primary tumor, and administration of the polypeptide fraction or the one or more polypeptides can reduce, inhibit or eliminate growth of metastasis.

Exemplary cancers that can be treated or prevented by contacting with the FWGP or one or more of the peptides or polypeptides of Table 1 include without limitation lymphoma, lung cancer, breast cancer, ovarian cancer, gastric and intestinal cancers (including colon cancer and rectal cancer), hepatic cancer, esophageal cancer, bladder cancer, renal cancer, head and neck cancers. In some embodiments, the cancer produces solid tumors. In some embodiments, the cancer is an epithelial cancer or a carcinoma, a sarcoma, or a hematological cancer.

Exemplary hematologic malignancies that can be treated or prevented by contacting with the FWGP or one or more of the peptides or polypeptides of Table 1 include without limitation lymphomas (such as but not limited to, non-Hodgkin's lymphoma, including Burkitt's lymphoma, and Hodgkin's lymphoma, as well as all subtypes associated with each), acute lymphocytic leukemia (ALL), chronic lymphocytic leukemia (CLL), acute myeloid leukemia (AML), chronic myeloid leukemia (CML), and adult T-cell leukemia lymphoma.

Exemplary lung cancers that can be treated or prevented by contacting with the FWGP or one or more of the peptides or polypeptides of Table 1 include without limitation adenocarcinoma, squamous carcinoma, bronchial carcinoma, broncoalveloar carcinoma, large cell carcinoma, small-cell carcinoma, non-small cell lung carcinoma and metastatic lung cancer refractory to conventional chemotherapy.

Exemplary hematological cancers that can be treated or prevented by contacting with the FWGP or one or more of the peptides or polypeptides of Table 1 include without limitation leukemia, multiple myeloma and plasmocytoma.

Exemplary sarcomas that can be treated or prevented by contacting with the FWGP or one or more of the peptides or polypeptides of Table 1 include without limitation rhabdomyosarcoma, osteosarcoma, chondrosarcoma, myosarcoma, liposarcoma, fibrosarcoma and Ewing's sarcoma.

Exemplary gastric, digestive and intestinal cancers that can be treated or prevented by contacting with the FWGP or one or more of the peptides or polypeptides of Table 1 include without limitation intestinal carcinoma, rectal carcinoma, colon carcinoma, familial adenomatous polyposis carcinoma, hereditary non-polyposis colorectal cancer, gastric carcinoma, craniopharyngioma, gall bladder carcinoma, esophageal carcinoma, pancreatic carcinoma and adenocarcinoma (including adenocarcinomas of the esophagus and stomach).

Exemplary cancers of the head and neck that can be treated or prevented by contacting with the FWGP or one or more of the peptides or polypeptides of Table 1 include without limitation larynx carcinoma, hypopharynx carcinoma, tongue carcinoma and salivary gland carcinoma.

Exemplary urogenital cancers that can be treated or prevented by contacting with the FWGP or one or more of the peptides or polypeptides of Table 1 include without limitation labial carcinoma, ovarian carcinoma, cervix carcinoma, uterine corpus carcinoma, endometrium carcinoma, chorion carcinoma, prostate carcinoma, testis carcinoma, seminoma, urinary carcinoma, kidney carcinoma, renal carcinoma, and adenocarcinoma (including adenocarcinomas of the vagina, cervix, prostate, and urachus).

Exemplary nervous and sensory system cancers that can be treated or prevented by contacting with the FWGP or one or more of the peptides or polypeptides of Table 1 include without limitation neuroblastoma, brain tumors, meningioma, ependymoma, medulloblastoma, peripheral neuroectodermal tumors, glioblastoma, astrocytoma, oligodendroglioma and retinoblastoma.

Exemplary endocrine and glandular tissue cancers that can be treated or prevented by contacting with the FWGP or one or more of the peptides or polypeptides of Table 1 include without limitation pancreatic carcinoma, medullary thyroid carcinoma, follicular thyroid carcinoma, anaplastic thyroid carcinoma, papillary thyroid carcinoma, pheochromocytoma, adrenal tumors and adenocarcinoma.

Exemplary hepatic cancers that can be treated or prevented by contacting with the FWGP or one or more of the peptides or polypeptides of Table 1 include without limitation hepatocellular carcinoma.

Exemplary skin cancers that can be treated or prevented by contacting with the FWGP or one or more of the peptides or polypeptides of Table 1 include without limitation melanoma, basal cell carcinoma, squamous cell carcinoima and choroids melanoma.

Additional cancers that can be treated or prevented by contacting with the FWGP or one or more of the peptides or polypeptides of Table 1 include without limitation teratomas.

6. Methods of Administering Polypeptides a. Routes of Administration

The FWGP or one or more of the peptides or polypeptides of Table 1 can be formulated into pharmaceutical formulations for administration to a patient. Administration of the pharmaceutical formulations can be by a variety of methods. Methods can include systemic administration, wherein the polypeptide or composition of polypeptides is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration, with the proviso that, as used herein, systemic administration does not include direct administration to the brain region by means other than via the circulatory system, such as intrathecal injection and intracranial administration. In other embodiments administration of the FWGP or one or more of the peptides or polypeptides of Table 1 is local, e.g., topically or intratumorally.

b. Dosing

The FWGP or one or more of the peptides or polypeptides of Table 1 can be administered for prophylactic and/or therapeutic treatments. In therapeutic applications, compositions comprising the FWGP or one or more of the peptides or polypeptides of Table 1 are administered to a patient suffering from a disease or malignant condition, such as cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health, and clinical studies are often done to determine the best dose for a given cancer type. An effective amount of the compound is that which provides either subjective relief of a symptom(s) or an objectively identifiable improvement as noted by the clinician or other qualified observer.

In prophylactic applications, compositions containing the FWGP or one or more of the peptides or polypeptides of Table 1 are administered to a patient not already in a disease state to prevent the onset of disease. Such an amount is defined to be a "prophylactically effective dose." In this use, the precise amounts again depend upon the patient's state of health.

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 11th Edition, 2006, supra; in a Physicians' Desk Reference (PDR), 64$^{th}$ Edition, 2010; in *Remington: The Science and Practice of Pharmacy,* 21$^{st}$ Ed., 2006, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

Exemplary doses of the pharmaceutical formulations described herein, include milligram or microgram amounts of the FWGP or one or more of the peptides or polypeptides of Table 1 per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of the FWGP or one or more of the peptides or polypeptides of Table 1 depend upon the potency of the composition with respect to the desired effect to be achieved. When the FWGP or one or more of the peptides or polypeptides of Table 1 are to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

The appropriate dosage of the polypeptides of the present invention will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

The dosage of FWGP or one or more of the peptides or polypeptides of Table 1 administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the FWGP or one or more of the peptides or polypeptides of Table 1, is a dosage that is sufficient to achieve the desired effect.

Optimum dosages, toxicity, and therapeutic efficacy of compositions can further vary depending on the relative potency of individual compositions and can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, $LD_{50}/ED_{50}$. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g., rodents and monkeys) can be used to formulate a dosage range for use in humans. The dosage of polypeptides of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a polypeptide or composition, is from about 1 ng/kg to 100 mg/kg for a typical subject.

A typical polypeptide composition of the present invention for intravenous administration would be about 0.1 to 10 mg/kg per patient per day. Dosages from 0.1 up to about 100 mg/kg per patient per day may be used. Actual methods for preparing administrable compositions will be known or apparent to those skilled in the art and are described in more detail in such publications as *Remington: The Science and Practice of Pharmacy*, 21$^{st}$ Ed., 2006, Lippincott Williams & Wilkins.

In one embodiment of the present invention, a pharmaceutical formulation of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 10 mg/kg.

Exemplary doses of the pharmaceutical formulations can include 100-500 mg daily doses as needed. Pharmaceutical formulations can be administered at a concentration of about 25 mg/mL to about 50 mg/mL. Exemplary doses of the pharmaceutical formulations can include about 50-200 mg/kg, for example, about 100 mg/kg daily doses.

Dosing can also be performed using comparative dosages, such as administering the FWGP or one or more of the peptides or polypeptides of Table 1 at a fraction of the dosage of the FWGE, wherein the lower dosage of the FWGP or one or more of the peptides or polypeptides of Table 1 results in similar prevention of inhibition of cancer cell growth to the higher FWGE dosage. Administration of FWGP or one or more of the peptides or polypeptides of Table 1 can be at $\frac{1}{5}^{th}$, $\frac{1}{10}^{th}$, $\frac{1}{15}^{th}$, $\frac{1}{20}^{th}$, $\frac{1}{30}^{th}$, $\frac{1}{40}^{th}$, $\frac{1}{50}^{th}$, $\frac{1}{60}^{th}$, $\frac{1}{75}^{th}$, $\frac{1}{80}^{th}$, $\frac{1}{90}^{th}$, $\frac{1}{100}^{th}$, $\frac{1}{150}^{th}$, $\frac{1}{200}^{th}$, $\frac{1}{500}^{th}$, $\frac{1}{1000}^{th}$, or lower when compared to the dosage of FWGE.

Following successful treatment, it may be desirable to have the subject undergo maintenance therapy to prevent the recurrence of the disease or malignant condition treated.

c. Scheduling

Optimal dosing schedules can be calculated from measurements of polypeptides in the body of a subject. In general, dosage is from 1 ng to 1,000 mg per kg of body weight and may be given once or more daily, semiweekly, weekly, biweekly, semimonthly, monthly, bimonthly or yearly, as needed or appropriate. Persons of ordinary skill in the art can easily determine optimum dosages, dosing methodologies and repetition rates. One of skill in the art will be able to determine optimal dosing for administration of a polypeptide or polypeptide composition of the present invention to a human being following established protocols known in the art and the disclosure herein.

The one or more polypeptides or peptides in the FWGP can be administered together or separately, e.g., as mixtures or in separate formulations. The FWGP or the one or more polypeptides of Table 1 can be administered via the same or different routes of administration. The FWGP or the one or more polypeptides of Table 1 can be administered concurrently or sequentially. Such scheduling is with respect to the other FWGP or the one or more polypeptides of Table 1, and other active agents for combination therapies.

Single or multiple administrations of the pharmaceutical formulations may be administered depending on the dosage and frequency as required and tolerated by the patient. In any event, the composition should provide a sufficient quantity of the polypeptides of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Thus, a pharmaceutical formulation thereof for intravenous administration would be about 0.01 to 100 mg/kg per patient per day. Dosages from 0.1 up to about 1000 mg/kg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington: The Science and Practice of Pharmacy*, 21$^{st}$ Ed., 2006, Lippincott Williams & Wilkins.

To achieve the desired therapeutic effect, pharmaceutical formulations may be administered for multiple days at the therapeutically effective daily dose. Thus, therapeutically effective administration of compositions to treat a disease or malignant condition described herein in a subject may require periodic (e.g., daily) administration that continues for a period ranging from three days to two weeks or longer. Typically, compositions will be administered for at least three consecutive days, often for at least five consecutive days, more often for at least ten, and sometimes for 20, 30, 40 or more consecutive days, or longer, as needed. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the composition in the subject. For example, one can administer a composition every other day, every third day, or, if higher dose ranges are employed and tolerated by the subject, once a week.

d. Combination Therapies with Established Anticancer Therapies i. Chemotherapy

The FWGP or one or more of the polypeptides of Table 1 can be co-administered with other agents as combination therapies. In some embodiments the FWGP or one or more of the polypeptides of Table 1 may be co-administered with one or more chemotherapeutic agent.

Examples of chemotherapeutic agents that can be co-administered with the FWGP or one or more of the polypeptides of Table 1 include without limitation alkylating agents (cisplatin, carboplatin, and oxaliplatin); anti-metabolites (purine or pyrimidine mimetics including for example azathioprine and mercaptopurine); plant alkaloids and terpenoids (vinca alkaloids and taxanes); vinca alkaloids (vincristine, vinblastine, vinorelbine, and vindesine); podophyllotoxin (including etoposide and teniposide); taxanes (paclitaxel, taxol and docetaxel); topoisomerase inhibitors (Type I inhibitors: camptothecins, irinotecan and topotecan; Type II Inhibitors: amsacrine, etoposide, etoposide phosphate, and teniposide); antineoplastics (dactinomycin, doxorubicin, epirubicin, fludarabine and bleomycin). Any chemotherapeutic agent being used to treat the cancer of interest can be co-administered in a combination therapy regime with the peptide and polypeptides of the FWGP or one or more of the polypeptides of Table 1.

ii. Immunotherapy

The FWGP or one or more of the polypeptides of Table 1 can be co-administered with one or more therapeutic antibodies as combination therapies.

Examples of therapeutic antibodies that can be co-administered with the FWGP or one or more of the polypeptides of Table 1 include but are not limited to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope); IgG antibody (ImClone System); IMC-C225 which is a chimeric anti-EGFR IgG antibody; VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 which is a humanized anti-ICAM3 antibody (ICOS Pharm); IDEC-114 which is a primate anti-CD80 antibody (IDEC Pharm/Mitsubishi); ZEVALIN™ which is a radiolabelled murine anti-CD20 antibody (IDEC/Schering AG); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); SMART anti-CD3 which is a humanized anti-CD3 IgG (Protein Design Lab); 5G1.1 which is a humanized anti-complement factor 5 (C5) antibody (Alexion Pharm); D2E7 which is a humanized anti-TNF-α antibody (CAT/BASF); CDP870 which is a humanized anti-TNF-α Fab fragment (Celltech); IDEC-151 which is a primatized anti-CD4 IgG1 antibody (IDEC Pharm/SmithKline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4,7 antibody (LeukoSite/Genentech); OrthoClone OKT4A which is a humanized anti-CD4 IgG antibody (Ortho Biotech); ANTOVA™ which is a humanized anti-CD40L IgG antibody (Biogen); ANTEGREN™ which is a humanized anti-VLA-4 IgG antibody (Elan); and CAT-152 which is a human anti-TGF-$\beta_2$ antibody (Cambridge Ab Tech).

Therapeutic antibodies that specifically bind to a tumor-associated antigen ("TAA") find use. Examples of known TAAs include without limitation, melanoma associated antigens (MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGβ) subunit expressed by many different tumors, including but not limited to myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B cell lymphoma can generate tumor-specific immunity (attributed to idiotype-specific humoral immune response). Moreover, antigens of human T cell leukemia virus type 1 have been shown to induce specific CTL responses and antitumor immunity against the virus-induced human adult T cell leukemia (ATL). See, e.g., Haupt, et al., *Experimental Biology and Medicine* (2002) 227:227-237; Ohashi, et al., *Journal of Virology* (2000) 74(20):9610-9616. Other TAAs are known and find use for co-administration with the FWGP or one or more of the polypeptides of Table 1.

iii. Radiation

The FWGP or one or more of the polypeptides of Table 1 can be administered in conjunction with radiological procedures. A variety of radiological procedures are available for disease treatments. Any of the procedures know by one of skill can be combined with the polypeptides of the present invention for treatment of a patient. Radiological procedures comprise treatment using radiation therapy to damage cellular DNA. The damage to the cellular DNA can be caused by a photon, electron, proton, neutron, or ion beam directly or indirectly ionizing the atoms which make up the DNA chain. Indirect ionization occurs due to the ionization of water, forming free radicals, notably hydroxyl radicals, which then subsequently damage the DNA. In the most common forms of radiation therapy, the majority of the radiation effect is through free radicals. Due to cellular DNA repair mechanisms, using agents that induce double-strand DNA breaks, such as radiation therapies, has proven to be a very effective technique for cancer therapy. Cancer cells are often undifferentiated and stem cell-like, such cells reproduce more rapidly and have a diminished ability to repair sub-lethal damage compared healthy and more differentiated cells. Further, DNA damage is inherited through cell division, leading to an accumulation of damage to the cancer cells, inducing slower reproduction and often death.

The amount of radiation used in radiation therapy procedure is measured in gray (Gy), and varies depending on the type and stage of cancer being treated and the general state of the patient's health. The dosage range can also be affected by cancer type, for example, the typical curative dosage for a solid epithelial tumor ranges from 60 to 80 Gy, while the dosage for lymphoma ranges from 20 to 40 Gy.

Preventative (adjuvant) doses can also be employed and typically range from 45 to 60 Gy administered in 1.8 to 2 Gy fractions (for breast, head and neck cancers). Many other factors are well-known and would be considered by those of skill when selecting a dose, including whether the patient is receiving other therapies (such as for example, but not limited to administration of the FWGP or one or more of the polypeptides of Table 1, administration of chemotherapies and the like), patient co-morbidities, timing of radiation therapy (for example, whether radiation therapy is being administered before or after surgery), and the degree of success of any surgical procedures.

Delivery parameters of a prescribed radiation dose can be determined during treatment planning by one of skill. Treatment planning can be performed on dedicated computers using specialized treatment planning software. Depending on the radiation delivery method, several angles or sources may be used to sum to the total necessary dose. Generally, a plan is devised that delivers a uniform prescription dose to the tumor and minimizes the dosage to surrounding healthy tissues.

iv. Surgery

The FWGP or one or more of the polypeptides of Table 1 can be administered in conjunction with surgical removal or debulking of tumors. A variety of surgical procedures are available for disease treatments. Any of the procedures know by one of skill can be combined with the polypeptides of the present invention for treatment of a patient. Surgical procedures are the commonly categorized by urgency, type of procedure, body system involved, degree of invasiveness, and special instrumentation.

Examples of surgical procedure can include emergency as well as scheduled procedures. Emergency surgery is surgery that must be done quickly to save life, limb, or functional capacity. Further examples of surgical procedures can include exploratory surgery, therapeutic surgery amputation, replantation, reconstructive, cosmetic, excision, transplantation or removal of an organ or body part, as well as others know in the art. Exploratory surgery can be performed to aid or confirm a diagnosis. Therapeutic surgery treats a previously diagnosed condition. Amputation involves cutting off a body part, usually a limb or digit. Replantation involves reattaching a severed body part. Reconstructive surgery involves reconstruction of an injured, mutilated, or deformed part of the body. Cosmetic surgery can done to improve the appearance of an otherwise normal structure or for repair of a structure damaged or lost due to disease. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

In addition to traditional open surgical procedure that employ large incisions to access the area of interest, surgery procedures further include minimally invasive surgery. Minimally invasive surgery typically involves smaller outer incision(s) which are employed for insertion of miniaturized instruments within a body cavity or structure, as in laparoscopic surgery or angioplasty. Laser surgery involves the use of a laser for cutting tissue instead of a scalpel or similar surgical instruments. Microsurgery involves the use of an operating microscope for the surgeon to see small structures. Robotic surgery makes use of a surgical robot (such as for example the Da Vinci (Intuit Surgical, Sunnyvale, Calif.)), to control the instrumentation under the direction of one of skill, such as for example a surgeon.

7. Methods of Monitoring Efficacy of Treatment and Prevention

A variety of methods can be employed in determining efficacy of therapeutic and prophylactic treatment with the polypeptides of the present invention. Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. The FWGP or the one or more polypeptides of Table 1 can be screened for prophylactic or therapeutic efficacy in animal models in comparison with untreated or placebo controls. The FWGP or the one or more polypeptides of Table 1 identified by such screens can be then analyzed for the capacity to induce tumor cell death or enhanced immune system activation. For example, multiple dilutions of sera can be tested on tumor cell lines in culture and standard methods for examining cell death or inhibition of cellular growth can be employed. (See, e.g., Maniatis, et al., *Molecular Cloning: A Laboratory Manual*, Cold Spring Harbor Lab., New York, 1982; Ausubel, et al. Editor, *Current Protocols in Molecular Biology*, USA, 1984-2008; and Ausubel, et al. Editor, *Current Protocols in Molecular Biology*, USA, 1984-2008; Bonifacino, et al., Editor, *Current Protocols in Cell Biology*, USA, 2010; all of which are incorporated herein by reference in their entirety.)

The methods of the present invention provide for detecting inhibition disease in patient suffering from or susceptible to various cancers. A variety of methods can be used to monitor both therapeutic treatment for symptomatic patients and prophylactic treatment for asymptomatic patients.

Monitoring methods entail determining a baseline value of a tumor burden in a patient before administering a dosage of FWGP or the one or more polypeptides of Table 1, and comparing this with a value for the tumor burden after treatment, respectively.

With respect to therapies using the FWGP or the one or more polypeptides of Table 1, a significant decrease (i.e., greater than the typical margin of experimental error in repeat measurements of the same sample, expressed as one standard deviation from the mean of such measurements) in value of the tumor burden signals a positive treatment outcome (i.e., that administration of the FWGP or the one or more polypeptides of Table 1 has blocked or inhibited, or reduced progression of tumor growth and/or metastasis).

In other methods, a control value of tumor burden (e.g., a mean and standard deviation) is determined from a control population of individuals who have undergone treatment with the FWGP or the one or more polypeptides of Table 1. Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant decrease in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can be analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

Further, the level of immune system activity in conjunction with tumor burden in a patient before administering a dosage of FWGP or the one or more polypeptides of Table 1 can be compared this with a value for the immune system activity in conjunction with tumor burden after treatment, again respectively.

With respect to therapies involving enhanced immune system activity, a significant increase (i.e., greater than the typical margin of experimental error in repeat measurements of the same sample, expressed as one standard deviation from the mean of such measurements) in value of immune response signals a positive treatment outcome (i.e., that administration of the FWGP or the one or more polypeptides of Table 1 has achieved or augmented an immune response). Immune response signals can include but are not limited to for example assessing the enhancement of the lymphoma-specific cytotoxic effect of human peripheral blood mononuclear cells (PBMCs). If the value for the immune response signal does not change significantly, or decreases, a negative treatment outcome is indicated. In general, patients undergoing an initial course of treatment with an immunogenic agent are expected to show an increase in immune response activity with successive dosages, which eventually reaches a plateau. Administration of an agent is often continued while the immune response is increasing. Once a plateau is obtained, that is an indicator if the treatment is solely for the immune the administration of the treatment can be discontinued or reduced in dosage or frequency.

8. Kits Comprising Fermented Wheat Germ Polypeptides

The present invention also provides for kits comprising the FWGP or the one or more polypeptides of Table 1. In some embodiments, the kits can contain two or more FWGP polypeptides, e.g., 2, 3, 4, 5, 6, 7, 8, 9, 10, 11, 12, 13, 14, 15, 16, 17, 18, 19, 20 or more polypeptides listed in Table 1. The two or polypeptides can be formulated in mixtures or as separate formulations. In some embodiments, the kits comprise all the polypeptides listed in Table 1, in one or more mixture, or in separate formulations.

The embodiments of the FWGP or the one or more polypeptides or peptides of Table 1 in the kits are as described herein. In some embodiments, the kits further comprise a therapeutic antibody, as described herein.

In addition the kits will typically include instructional materials disclosing means of use of the FWGP or the one or more polypeptides or peptides of Table 1. The kits may also include additional components to facilitate the particular application for which the kit is designed. The kits may additionally include buffers and other reagents routinely used for the practice of a particular method. Such kits and appropriate contents are well known to those of skill in the art.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are offered to illustrate, but not to limit the claimed invention.

Example 1

Production of Fermented Wheat Germ Extract and FWGP 100 g of fresh wheat germ (Northern Edge brand, Randolph & James Flax Mills Ltd, Prince Albert, Saskatchewan, Canada) was dry-blended to flour quality, then mixed with one liter of distilled water and 33.3 g of a Baker's yeast (Sigma). The mixture was shaken at 250 rpm at 30° C. for 42-48 hours, and centrifuged at 2,000 g for 15 minutes. The supernatant was collected and freeze-dried to yield powder of fermented wheat germ extract (FWGE).

Fractionation and Purification of Fermented Wheat Germ Extract

To purify the components of FWGE, soluble proteins from the supernatant obtained as described above was precipitated in 75% ethanol at 4° C. The precipitate was dissolved in PBS and the solution was passed through a Sephadex G50 column. The eluent was collected, vacuum-dried overnight and re-dissolved in PBS. The solution was passed through a Superdex S200 column. Elution fractions, with molecular weights ranging from 10,000 to 100,000, were collected, combined and vacuum-dried overnight. The dry powder was designated as fermented wheat germ proteins (FWGP). The eluent fractions were analyzed with SDS polyacrylamide gel electrophoresis (PAGE). The majority of the eluents were proven to be within the molecular weights of 10 to 100 Kd as shown in the following acrylamide gel (FIG. 1). Alternatively, FWGP could also be obtained, according to the procedures described above, by using a commercially available FWGE, Ave' (American BioSciences, Blauvelt, N.Y.).

Figure 2:
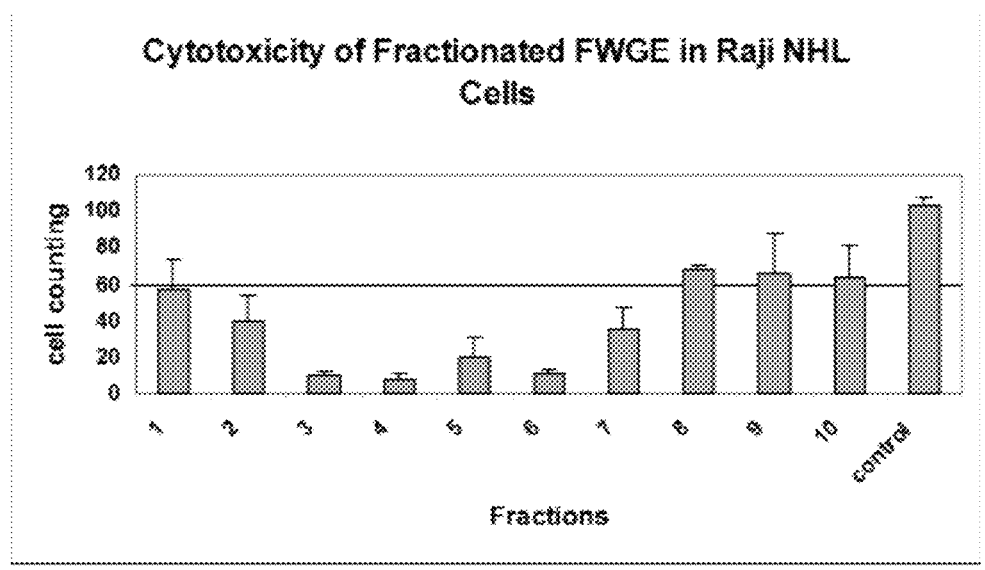
FIG. 2 illustrates fractionated FWGE was assessed for cytotoxicity in Raji NHL cells using trypan blue exclusion. Assays were done in triplicate with error bars representing standard deviation (SD).
Figure 3:
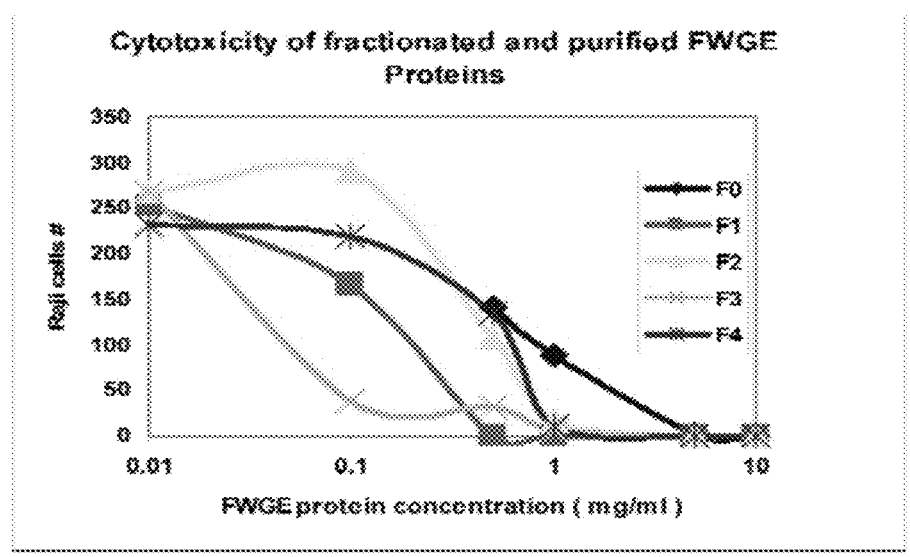
FIG. 3 illustrates the various fractions (described in FIG. 2) were assayed for cytotoxic potential and dose-response effect in Raji lymphoma cells.
Figure 4:
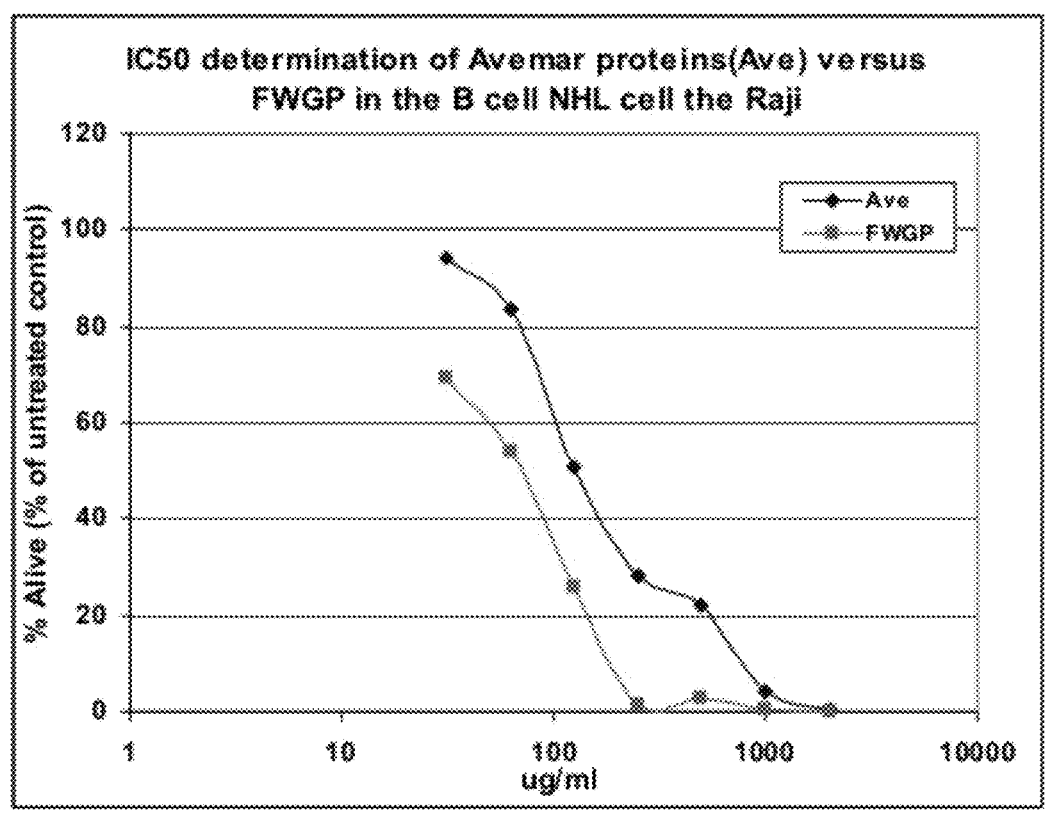
FIG. 4 illustrates comparison of the cytotoxic potential of FWGP that are derived from Avemar (Ave) or in lab-produced FWGE using Raji NHL cells. Raji is a B-cell line. Done as described in FIG. 2.
Figure 5:
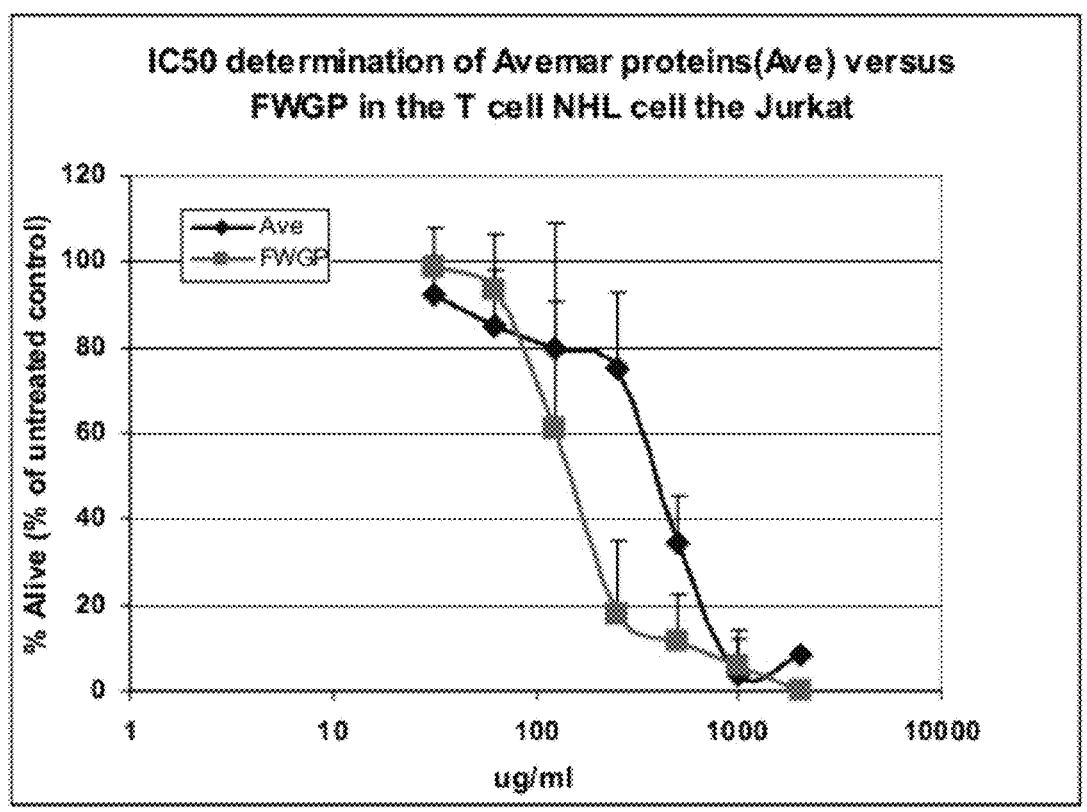
FIG. 5 illustrates comparison of the cytotoxic potential of FWGE that are derived from Avemar (Ave) versus in lab-produced FWGP using Jurkat T-cell NHL cells. Done as described in FIG. 2.

The cytotoxic potential of the fractionated FWGE was assessed using Raji lymphoma (NHL) cell line (FIGS. 2-3). Data in FIGS. 2 and 3 show that the purification method allowed isolation and identification of fractions of FWGE that had more potent cytotoxic effects than the parent extract. The cytotoxic potential of the purified extract was compared depending on the source (fermented in our laboratory versus a commercial source, Avemar), FIGS. 4 and 5.

Figure 6:
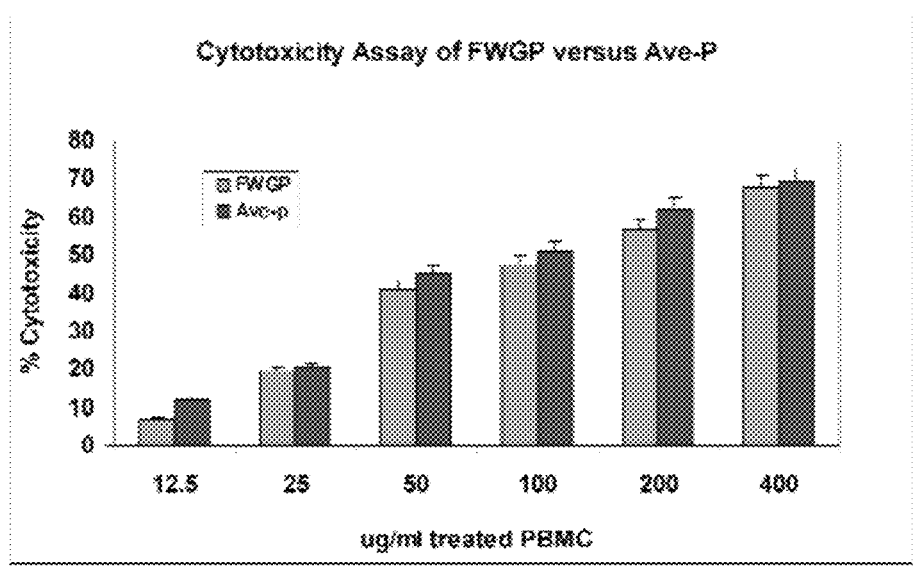
FIG. 6 illustrates Human PBMCs were incubated with indicated concentrations of FWGP either derived from in-house or commercially available FWGE (Avemar) for 20 hours, washed and incubated with Raji NHL cells at a PBMC:NHL cell ratio of 10:1. Target NHL-specific lysis was detected as previous described.
Figure 7:
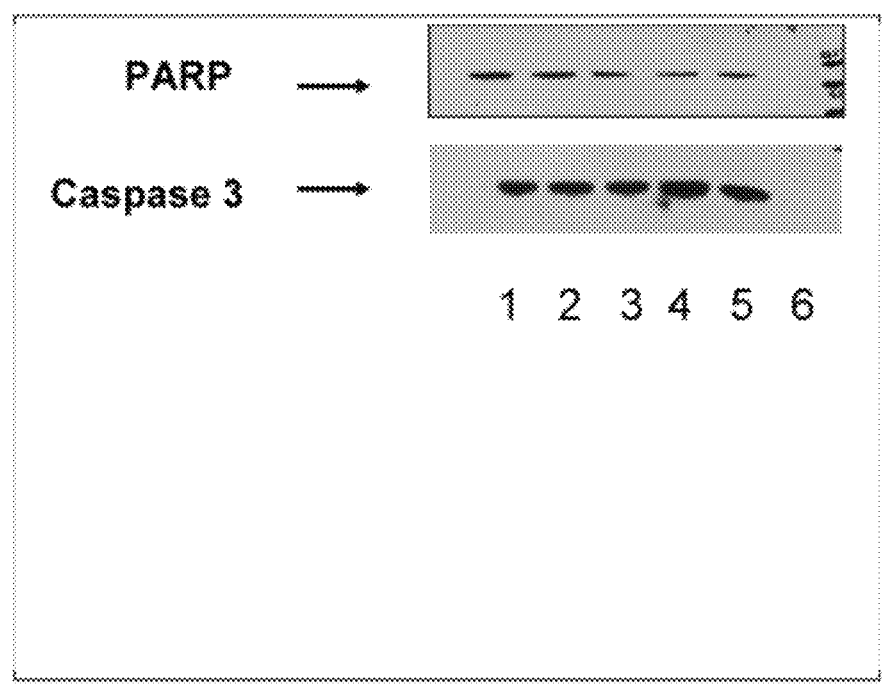
FIG. 7 illustrates both FWGP derived from Avemar or in-house produced FWGE induced activated caspase 3 and PARP. FWGP (500 ug) derived from Avemar (lanes 1 &2) or in-house produced FWGP (lanes 3 &4) were incubated with Ramos (B-cell) NHL cells. Whole cell lysates were assessed for PARP and activated caspase 3 by immunoblot analysis. This was compared to untreated (lane 6) or a positive control, anti-IgM (50 ug) (lane 5).

These and other experiments demonstrate that the cytotoxic effects of FWGPs are similar irrespective of the source of FWGE. The potential of FWGPs to enhance the lymphoma-specific cytotoxic effect of human peripheral blood mononuclear cells (PBMCs) was assessed. Human PBMCs were incubated with various but equivalent amounts of FWGPs derived from Avemar or in-house generated FWGE, FIG. 6. This demonstrated that both sources FWGPs were able to activate human PBMCs and significantly augment PBMC-mediated NHL cell killing. The mechanism of FWGP-mediated NHL cell killing is via apoptosis. The mechanism of apoptotic induction was examined as well as whether apoptosis was dependent on the source of FWGE. Both sources of FWGE were assessed for poly (ADP-ribose) polymerase 1 (PARP1) and caspase 3 induction. Both PARP and caspase 3 were induced to an equivalent degree regardless of the source of FWGE, FIG. 7. These data confirm that FWGP can be derived from various FWGE sources.

Figure 8:
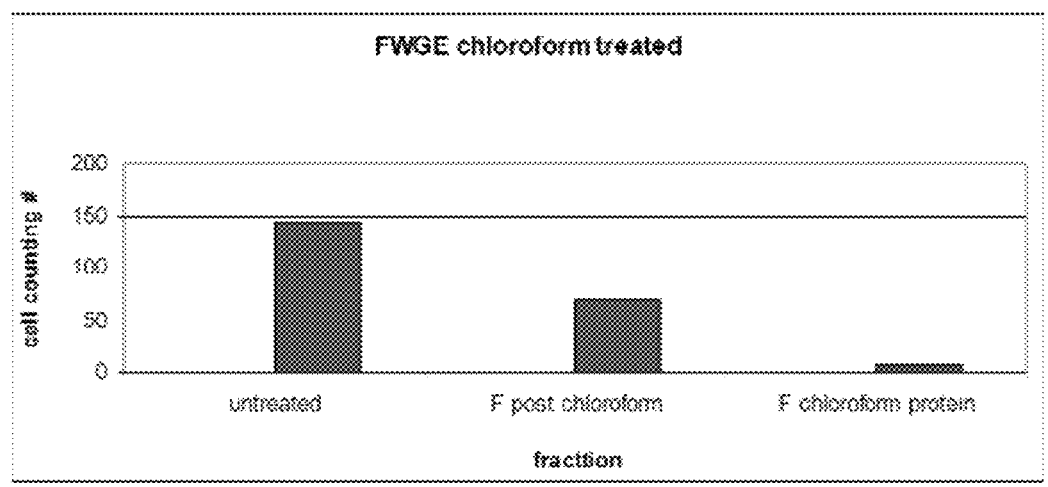
FIG. 8 illustrates FWGP was incubated with chloroform (50%) for 2 hours. Chloroform was then removed by extraction. Chloroform-treated FWGP (100 ug/ml) was assayed for cytotoxicity in Raji NHL cells as described in FIG. 2
Figure 9:
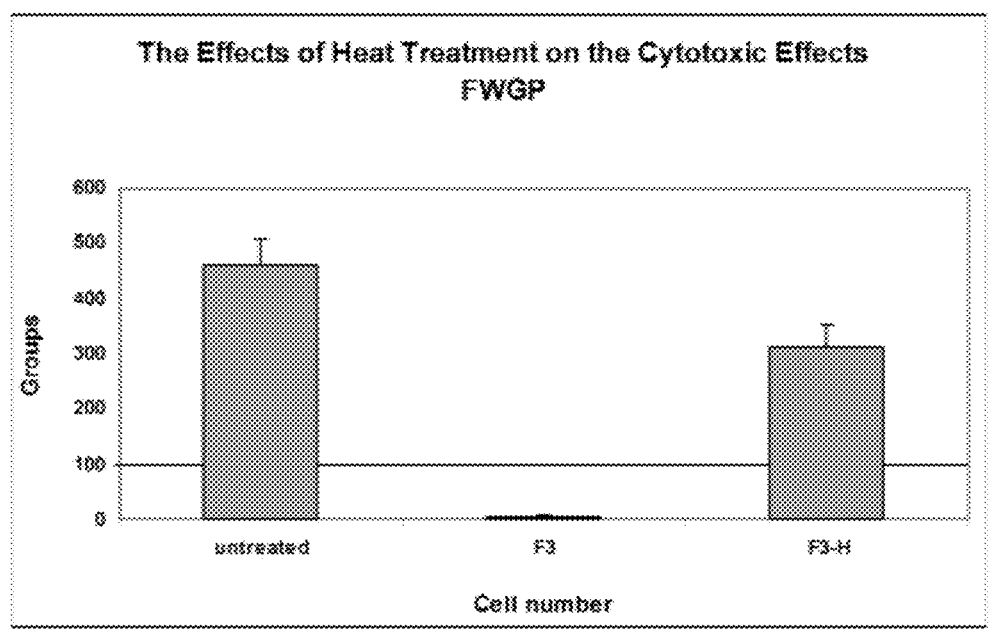
FIG. 9 illustrates fraction 3 (F3) of FWGP was heated to 100° C. for 70 minutes (F3-H) and then assayed for cytotoxicity using Raji NHL cells.
Figure 10:
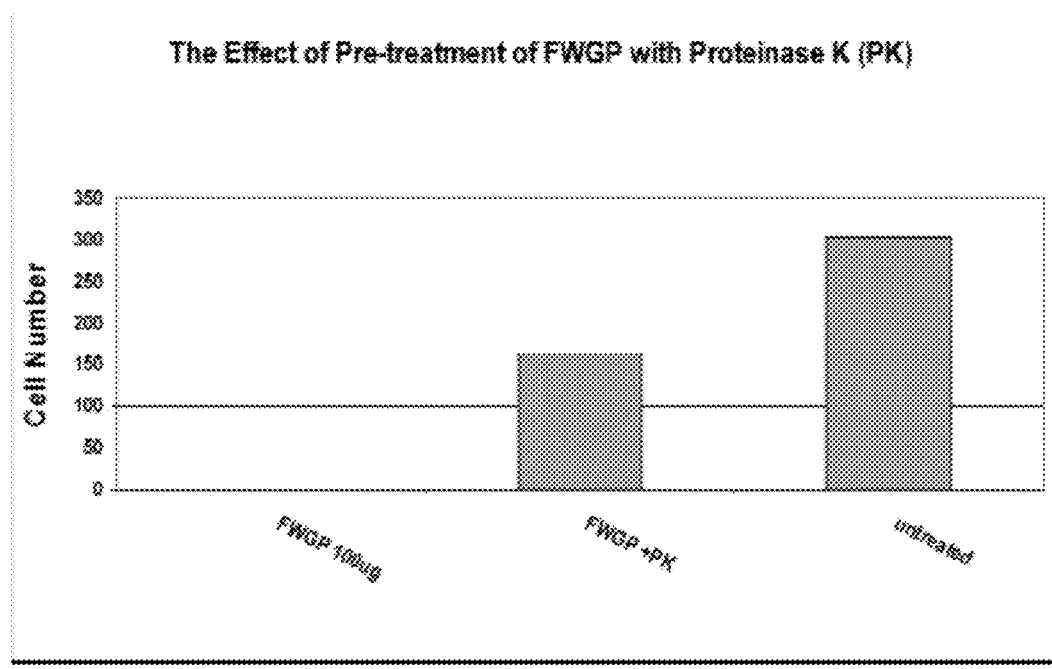
FIG. 10 illustrates FWGP was incubated with 100 ug of proteinase K (PK) for 2 hours at 56° C. The PK was then deactivated by subsequently heating to 95° C. for 20 minutes. PK treated and untreated FWGP was then assayed for cytotoxic activity using Raji NHL cells as described in FIG. 2.

Next the composition of FWGE and FWGP were examined by pre-incubation with chloroform, heat treatment, or proteinase K, FIGS. 8-10.

Figure 11:
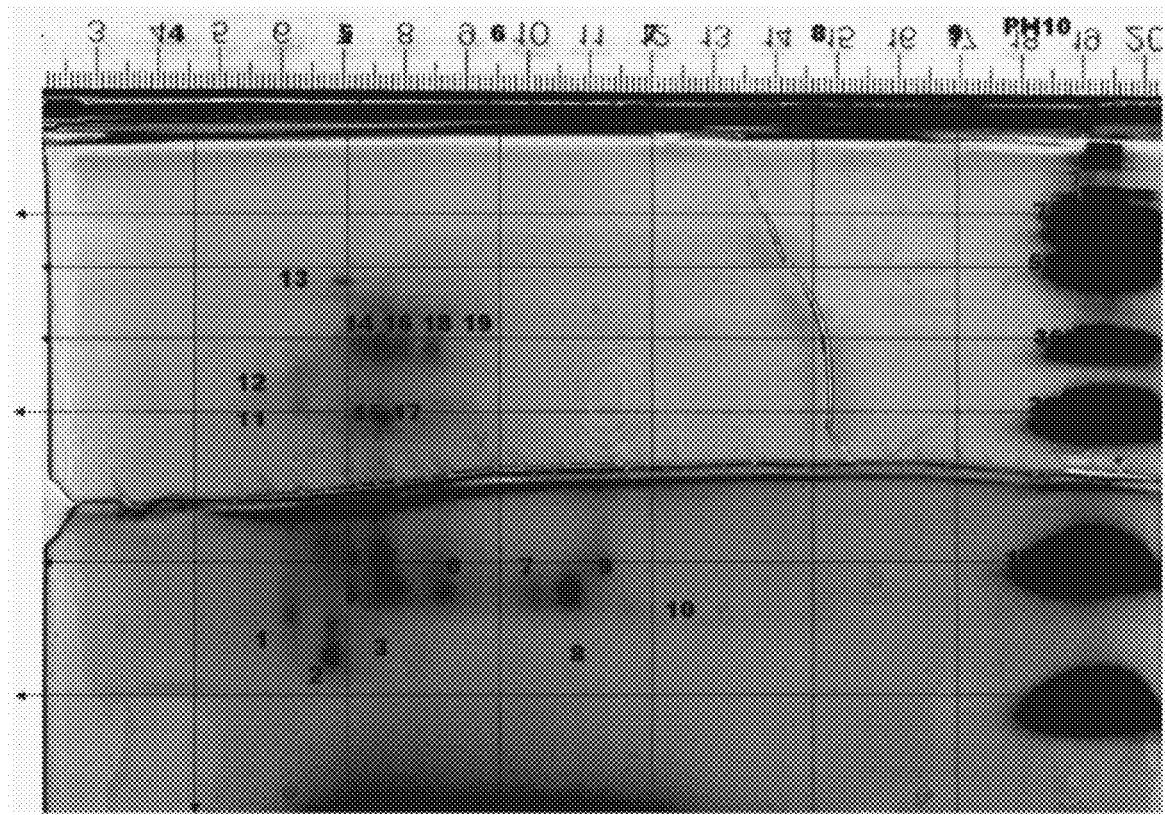
FIG. 11 illustrates FWGP was size and charge/Ph separated using 2D PAGE. Proteins were visualized by silver stain. Nineteen candidate proteins were identified. This gel is representative of replicate experiments with both Avemar-derived, and FWGE-derived FWGP.

This data confirms that a significant component of FWGP that produces its cytotoxic activity is protein. Next a two dimensional gel electrophoresis was used to identify the protein components of FWGP, FIG. 11. This study was reproducible with both Avemar and lab-produced FWGE-derived FWGP. Nineteen proteins were identified, excised, extracted, and subjected to mass spectral analysis. Database analysis revealed very little human or other protein contamination (the vast majority were native wheat proteins), and are listed in Table 1. Two of the proteins (wheat aspartic acid proteinase-1, and copper zinc superoxide dismutase) were subcloned and recombinant protein was generated. B-cell binding and cytotoxic potential was verified by flow cytometry and cytotoxicity assays (data not shown). Next the in vitro cytotoxic activity of FWGP was assessed in a panel of human cancer cell lines, Table 2.

TABLE 2

FWGP identified by mass spectral analysis

| Spot | PI | MW (Kd) | Proteins |
|---|---|---|---|
| 1 | 4.6 | 13 | early-methionine-labelled polypeptide; wheat aspartic proteinase-1; late embryogenesis abundant protein; thioredoxin h |
| 2 | 4.8 | 12 | Em protein H2; early-methionine-labelled polypeptide; thioredoxin h; late embryogenesis abundant protein |
| 3 | 4.8 | 13 | thioredoxin H-type; translational inhibitor protein; copper zinc-superoxide dismutase; translational inhibitor protein |
| 4 | 5.3 | 17 | copper zinc-superoxide dismutase; early-methionine-labelled polypeptide, |
| 5 | 5.3 | 16 | dimeric alpha-amylase inhibitor; translational inhibitor protein; late embryogenesis abundant protein |
| 6 | 5.6 | 16 | wsi18 protein induced by water stress; reversibly glycosylated polypeptide; early-methionine-labelled polypeptide |
| 7 | 6.2 | 16 | cold shock protein-1; hageman factor inhibitor; protein disulfide isomerase, |
| 8 | 6.5 | 16 | n-acetylneuraminyllactose-wheat germ agglutinin isolectin complexes; hageman factor inhibitor |
| 9 | 6.7 | 18 | copper zinc-superoxide dismutase; cold shock protein-1 |
| 10 | 6.9 | 15 | pathogenesis-related protein 5; dimeric alpha-amylase inhibitor |
| 11 | 4.6 | 28 | aspartic proteinase; secreted protein; early-methionine-labelled polypeptide |
| 12 | 4.6 | 30 | aspartic proteinase; desiccation-related protein pcc13-62 |
| 13 | 5.0 | 50 | high molecular weight glutenin subunit; reversibly glycosylated polypeptide |
| 14 | 5.2 | 36 | group 3 late embryogenesis abundant protein; serpin; late embryogenesis abundant protein |
| 15 | 5.2 | 27 | carboxymethylenebutenolidase; d-ribulose-5-phosphate 3-epimerase secreted protein; aspartic proteinase |

TABLE 2-continued

FWGP identified by mass spectral analysis

| Spot | PI | MW (Kd) | Proteins |
|---|---|---|---|
| 16 | 5.4 | 36 | serpin; lea protein; late embryogenesis abundant protein |
| 17 | 5.4 | 27 | carboxymethylenebutenolidase-like protein; d-ribulose-5-phosphate 3-epimerase; early-methionine-labelled polypeptide |
| 18 | 5.5 | 36 | late embryogenesis abundant protein; lea protein; secreted protein |
| 19 | 5.6 | 36 | group 3 late embryogenesis abundant protein |

TABLE 3

IC50 Assay of Human Tumor Cell Lines Treated with FWGP (72 hours) by MTT

| Cell Line | Tumor Type | IC50 (ug/ml) |
|---|---|---|
| H1650 | Lung | 144 |
| MCF-7 | Breast | 639 |
| HepG2 | Hepatic | 245 |
| Sudhl4 | NHL (diffuse large cell) | 70 |
| DG75 | Lymphoblastoid | 20 |
| BM35 | NHL (aggressive) | 71 |
| DoHH2 | NHL (follicular) | 171 |
| Raji | NHL (Burkitt's) | 39 |
| Ramos | NHL (Burkitt's) | 70 |
| WSU-WM | NHL/Waldenstroms | 82 |
| Granta-519 | NHL (mantle cell) | 80 |
| Chevalier | NHL | 40 |
| A549 | Lung | 70 |
| Hct-116 | Colon | 8 |

Figure 12:
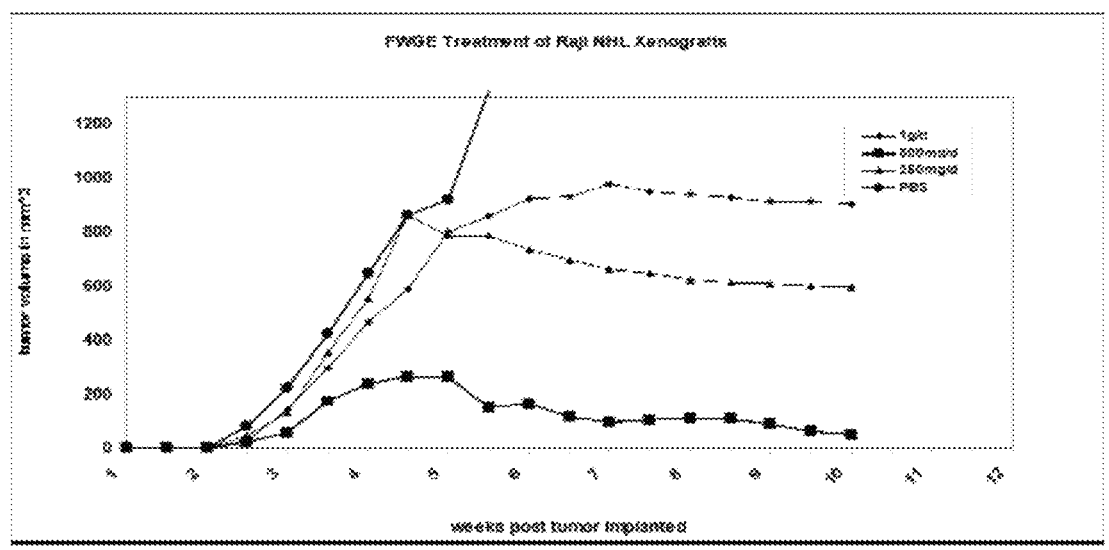
FIG. 12 illustrates nude mice bearing Raji xenografts were treated with daily oral FWGE at the indicated doses for 12 weeks.
Figure 13:
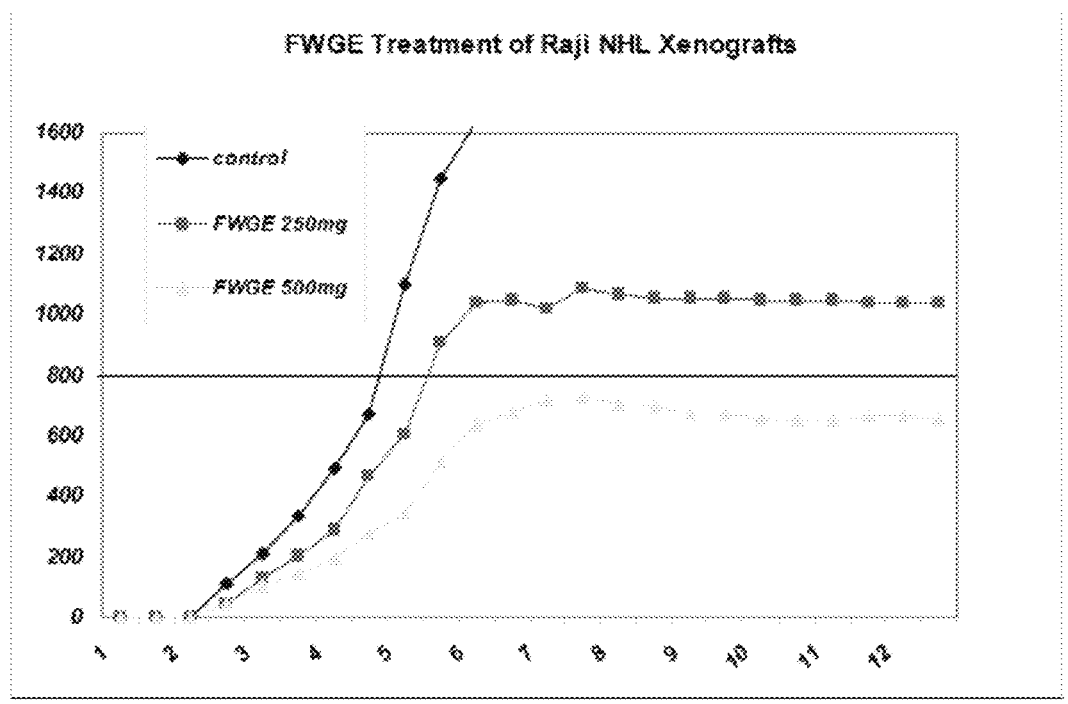
FIG. 13 illustrates nude mice bearing human NHL (Raji) xenografts were treated with daily oral FWGE at the indicated doses for 12 weeks.
Figure 14:
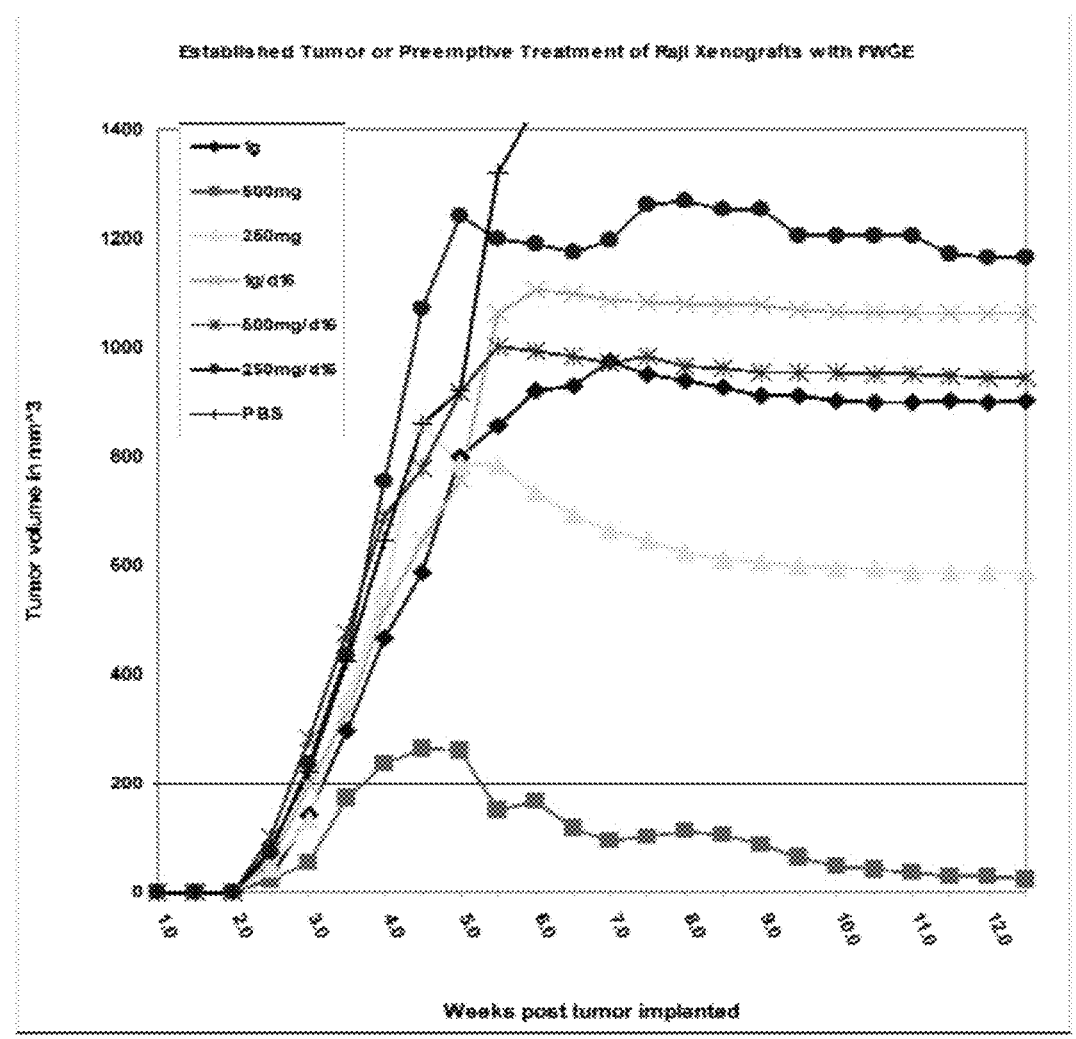
FIG. 14 illustrates nude mice bearing human NHL (Raji) xenografts were treated with oral FWGE at the indicated doses preemptively (treatment starting on the day of tumor implantation) or 16 days after (d16).

The data in Table 2 demonstrates that FWGP has significant and consistent in vitro cytotoxic activity in a broad range of tumor types. The in vivo efficacy of FWGE was examined in human NHL xenograft models using the Raji cell line, FIGS. 12-14. Theses studies demonstrated consistent efficacy that improved when the dose was increased to 500 mg/d, but began to decline when a dose over 500 mg was used. This was verified in several subsequent xenograft studies done as described above. Additional experiments in which mice bearing more established tumors were treated (treatment initiated 16 days after tumor implantation) and compared to preemptive therapy also demonstrated significant efficacy, FIG. 14. Next the efficacy of FWGE was compared to fractionated and purified FWGP, FIG. 15.

Figure 15:
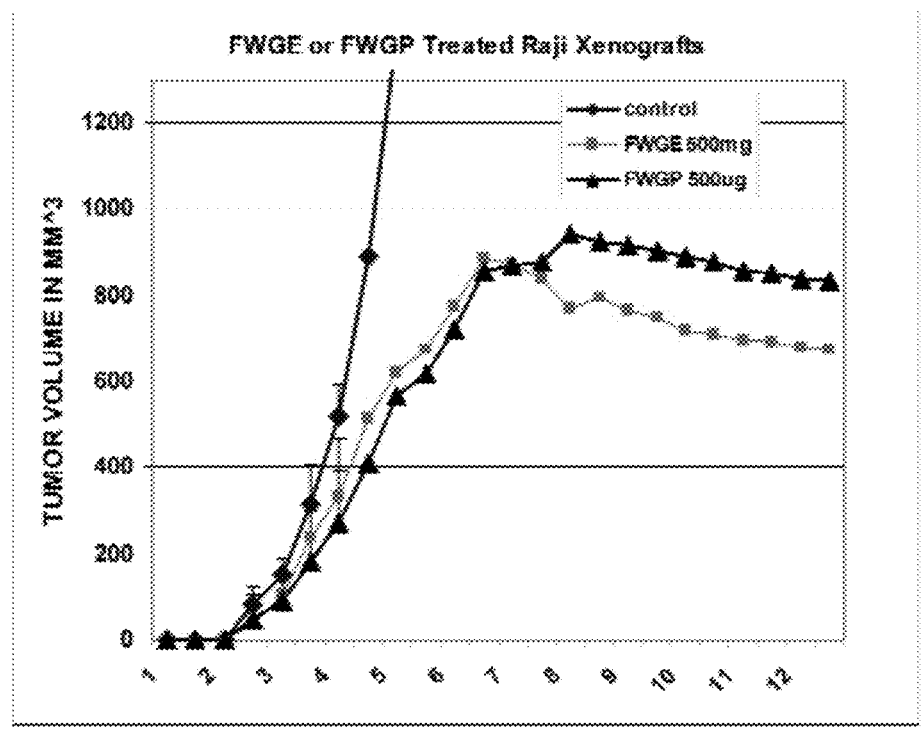
FIG. 15 illustrates nude mice bearing Raji xenografts were treated with daily oral FWGE or FWGP at indicated doses for 12 weeks.
Figure 16:
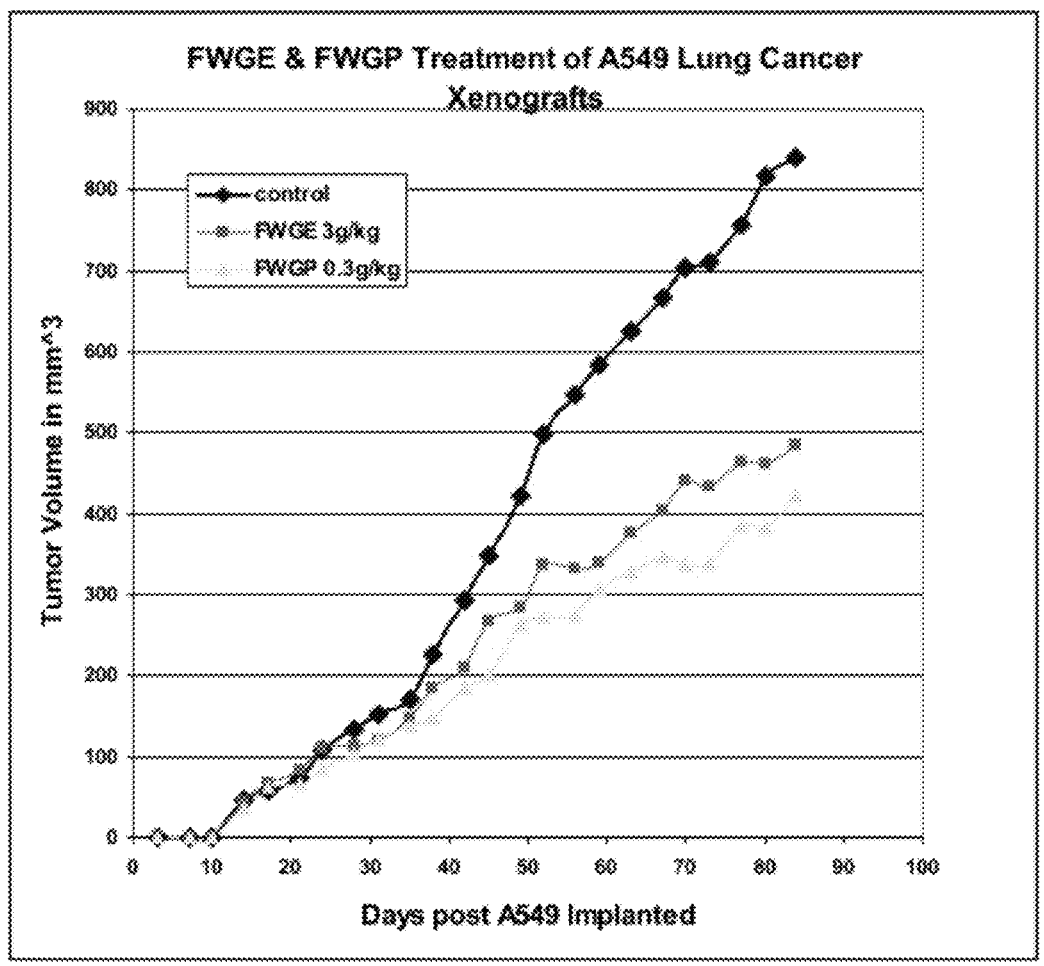
FIG. 16 illustrates nude mice bearing A549 xenografts were treated with daily oral FWGE or FWGP at doses described in FIG. 14 for 12 weeks.
Figure 17:
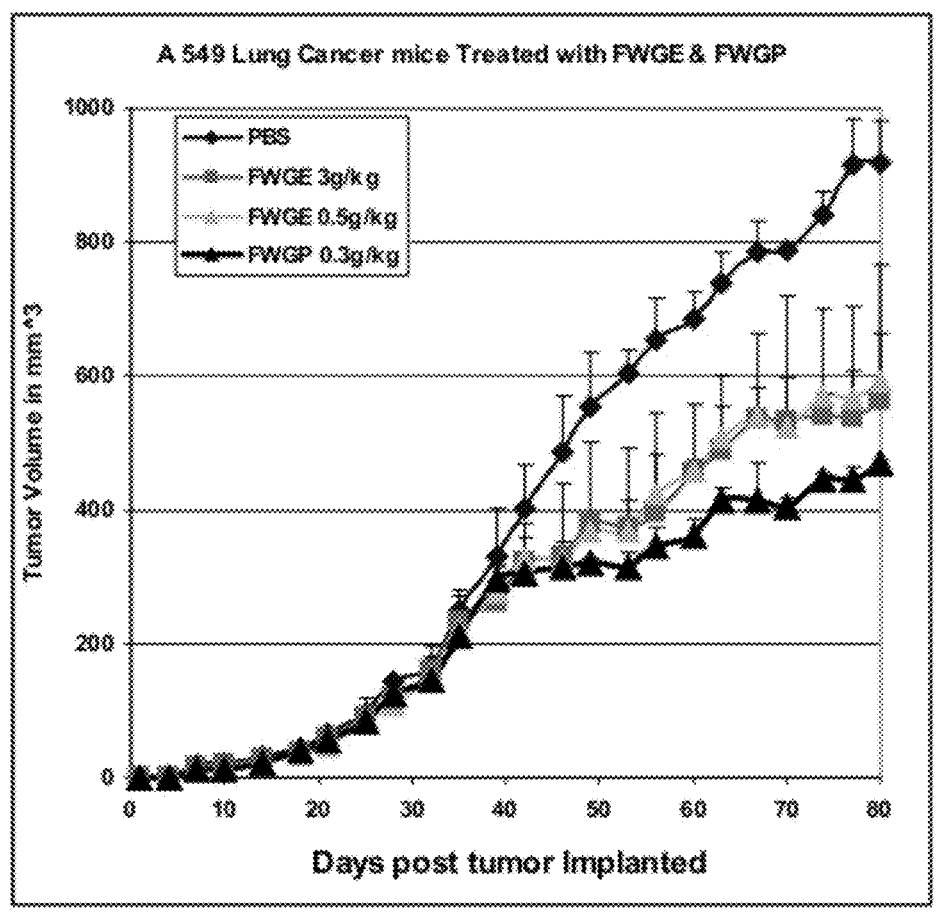
FIG. 17 illustrates nude mice bearing A549 xenografts were treated with daily oral FWGE or FWGP at indicated doses for 12 weeks.

These experiments verified the efficacy of FWGE and confirmed that the purified from (FWGP) had similar efficacy at $1/1000^{th}$ the dose, FIG. 15. Next the efficacy of FWGE and FWGP was assessed in a human lung xenograft model using the A549 lung cancer cell line, FIGS. 16 and 17. Treatment with FWGE and FWGP was non-toxic in all xenograft trials. Toxicity was assessed by mouse activity, daily weights, and blood counts.

The data in Experiments 16 and 17 verified that FWGE and FWGP had significant in vivo efficacy in a human lung cancer model. Next the mechanism of action of FWGP was further examined by evaluating its effects on human complement activation. A total complement activation assay was preformed after incubating FWGE or FWGP in human serum for 0.5, 3 and 24 hours, Table 3. This revealed that both FWGE and FWGP were potent complement activators. Based on this and the data that demonstrated the FWGP also mediated NHL-directed human PBMC-mediated cytotoxicity, (FIG. 5), the effects of FWGP on rituximab-mediated NHL-specific cytotoxicity was assessed, Table 4.

TABLE 4

Total Complement (CH50) Assay

| Time | 0.5 hr | 3 hr | 24 hr |
|---|---|---|---|
| Untreated | 50 U | 22 U | 17 U |
| FWGE 5 mg/ml | 50 U | 20 U | 0 U |
| FWGP 100 ug/ml | 40 U | 10 U | 0 U |

TABLE 5

| Groups | IC50 µg/ml | Concentration | Fold increase |
|---|---|---|---|
| FWGP | 108.13 | 30 ug/ml | — |
| Rituximab | 41.07 | 50 ug/ml | 2.6 |
| FWGP + rituximab | 1.46 | 30 ug/ml + 50 ug/ml | 74 |
| Rituximab + 1% HSC | 0.126 | | 860 |
| FWGP + rituximab + 1% HSC | 0.023 | | 4500 |

Figure 18:
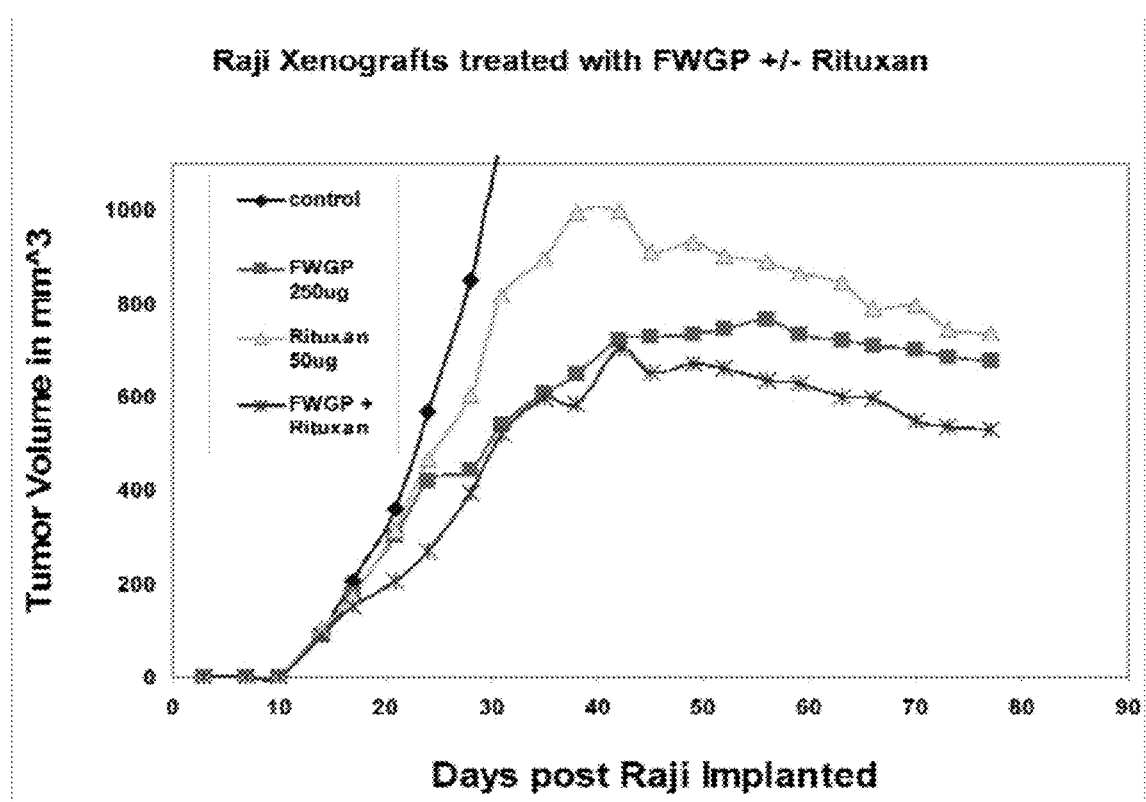
FIG. 18 illustrates nude mice bearing Raji xenografts were treated with daily, oral, FWGP with or without rituximab at indicated doses for 12 weeks.

The data in Table 5 verified that FWGP enhanced the cytotoxicity of rituximab by 4500 fold when combined with human serum complement (HSC). Based on this the efficacy of combining FWGP with rituximab was assessed in vivo using the same Raji model, FIG. 18. This verified that FWGP enhanced the in vivo efficacy of rituximab.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A composition comprising one or more polypeptides selected from wheat aspartic acid proteinase-1 and wheat copper zinc superoxide dismutase, and a pharmaceutically acceptable excipient, wherein the one or more polypeptides are at least about 80% purified, separated or isolated from non-proteinaceous components of FWGE.

2. A composition comprising fermented wheat germ extract polypeptides (FWGP), and a pharmaceutically acceptable excipient, wherein the FWGP is at least about 90% purified, separated or isolated from non-proteinaceous components of FWGE.

3. The composition of claim 2, wherein the FWGP is at least about 95% or 99% purified, separated or isolated from non-proteinaceous components of FWGE.

4. The composition of claim 2, wherein the FWGP is free of non-proteinaceous components of FWGE.

5. A method of reducing and/or inhibiting the growth and/or proliferation of a cancer cell, the method comprising contacting the cancer cell with one or more polypeptides selected from wheat aspartic acid proteinase-1 and wheat copper zinc superoxide dismutase, wherein the cancer is selected from the group consisting of lymphoma, lung cancer, breast cancer, colon cancer, and hepatic cancer, wherein the one or more polypeptides are at least about 80% purified, separated or isolated from non-proteinaceous components of fermented wheat germ extract (FWGE).

6. The method of claim 5, wherein the one or more polypeptides have been subject to fermentation.

7. The method of claim 5, further comprising contacting the cancer cell with one or more wheat polypeptides selected from the group consisting of early-methionine-labelled polypeptide, late embryogenesis abundant protein, FGAS022985 (Triticum aestivum FGAS: Library 6 CAP GATE 1), thioredoxin h, Em protein H2, translational inhibitor protein (Triticum aestivum FGAS: Library 4 Gate 8), FGAS051302 (Triticum aestivum FGAS: TaLt7), dimeric alpha-amylase inhibitor, G468.105F06R010929 G468 (Triticum aestivum cDNA clone G468105F06), wsi18 protein induced by water stress, reversibly glycosylated polypeptide, FGAS014876 (Triticum aestivum FGAS: Library 4 Gate 8), cold shock protein-1, FGAS021443 (Triticum aestivum FGAS: Library 5 GATE 7), subunit CM3 of alpha-amylase tetrameric inhibitor (hageman factor inhibitor), FGAS030061 (Triticum aestivum FGAS: Library 6 CAP GATE 1), protein disulfide isomerase, wheat germ agglutinin isolectin D, wheat germ agglutinin isolectin A, n-acetyl-neuraminyllactose-wheat germ agglutinin isolectin complexes, FGAS029900 Triticum aestivum FGAS: Library 6 CAP GATE 1), FGAS021317 (Triticum aestivum FGAS: Library 5 GATE 7), desiccation-related protein pcc13-62, BRY_901 BRY (Triticum aestivum cDNA clone P10-1L), high molecular weight glutenin subunit, FGAS014507 (Triticum aestivum FGAS: Library 4 Gate 8), group 3 late embryogenesis abundant protein, serpin, FGAS045291 (Triticum aestivum FGAS: TaLt6), carboxymethylen-ebutenolidase, carboxymethylenebutenolidase-like protein, FGAS075594 (Triticum aestivum FGAS: Library 2 Gate 3), G608.105K18F010906 G608 (Triticum aestivum cDNA clone G608105K18), ABA-inducible protein WRAB1, WHE2989_H12_P23ZS Wheat dormant embryo (Triticum aestivum cDNA clone WHE2989_H12_P23, Triticum aestivum LEA1 protein (LEA1), Triticum aestivum LEA2 protein (LEA2), Triticum aestivum LEA3 protein (LEA3), FGAS017876 (Triticum aestivum FGAS: Library 5 GATE 7), pathogenesis-related protein 5, and d-ribulose-5-phosphate 3-epimerase secreted protein.

8. The method of claim 5, further comprising contacting the cancer cell with a chemotherapeutic agent and/or an antibody against a tumor associated antigen.

9. The method of claim 5, wherein the cancer cell is in vivo.

10. The method of claim 5, wherein the cancer cell is in vitro.

11. The method of claim 5, wherein the cancer is a lymphoma.

12. The method of claim 5, wherein the cancer is a lung cancer.

13. The method of claim 5, wherein the one or more polypeptides are at least about 85%, 90% or 95% purified, separated or isolated from or free of non-proteinaceous components of FWGE.

14. A method of reducing and/or inhibiting the growth and/or proliferation of a cancer cell in a subject, the method comprising administering to the subject an effective amount of one or more polypeptides selected from wheat aspartic acid proteinase-1 and wheat copper zinc superoxide dismutase, wherein the cancer is selected from the group consisting of lymphoma, lung cancer, breast cancer, colon cancer, and hepatic cancer, wherein the one or more polypeptides are at least about 80% purified, separated or isolated from non-proteinaceous components of FWGE.

15. The method of claim 14, wherein the cancer is a lymphoma.

16. The method of claim 14, wherein the cancer is a lung cancer.

17. The method of claim 14, further comprising co-administering the one or more polypeptides with a chemotherapeutic agent and/or an antibody against a tumor associated antigen.

18. The method of claim 14, wherein further comprising co-administering one or more wheat polypeptides selected from the group consisting of early-methionine-labelled polypeptide, late embryogenesis abundant protein, FGAS022985 (*Triticum aestivum* FGAS: Library 6 CAP GATE 1), thioredoxin h, Em protein H2, translational inhibitor protein (*Triticum aestivum* FGAS: Library 4 Gate 8), FGAS051302 (*Triticum aestivum* FGAS: TaLt7), dimeric alpha-amylase inhibitor, G468.105F06R010929 G468 (*Triticum aestivum* cDNA clone G468105F06), wsi18 protein induced by water stress, reversibly glycosylated polypeptide, FGAS014876 (*Triticum aestivum* FGAS: Library 4 Gate 8), cold shock protein-1, FGAS021443 (*Triticum aestivum* FGAS: Library 5 GATE 7), subunit CM3 of alpha-amylase tetrameric inhibitor (hageman factor inhibitor), FGAS030061 (*Triticum aestivum* FGAS: Library 6 CAP GATE 1), protein disulfide isomerase, wheat germ agglutinin isolectin D, wheat germ agglutinin isolectin A, n-acetyl-neuraminyllactose-wheat germ agglutinin isolectin complexes, FGAS029900 (*Triticum aestivum* FGAS: Library 6 CAP GATE 1), FGAS021317 (*Triticum aestivum* FGAS: Library 5 GATE 7), desiccation-related protein pcc13-62, BRY_901 BRY (*Triticum aestivum* cDNA clone P10-1L), high molecular weight glutenin subunit, FGAS014507 (*Triticum aestivum* FGAS: Library 4 Gate 8), group 3 late embryogenesis abundant protein, serpin, FGAS045291 (*Triticum aestivum* FGAS: TaLt6), carboxymethylenebutenolidase, carboxymethylenebutenolidase-like protein, FGAS075594 (*Triticum aestivum* FGAS: Library 2 Gate 3), G608.105K18F010906 G608 (*Triticum aestivum* cDNA clone G608105K18), ABA-inducible protein WRAB1, WHE2989_H12_P23ZS Wheat dormant embryo (*Triticum aestivum* cDNA clone WHE2989_H12_P23, *Triticum aestivum* LEA1 protein (LEA1), *Triticum aestivum* LEA2 protein (LEA2), *Triticum aestivum* LEA3 protein (LEA3), FGAS017876 (*Triticum aestivum* FGAS: Library 5 GATE 7), pathogenesis-related protein 5, and d-ribulose-5-phosphate 3-epimerase secreted protein.

19. The method of claim 14, wherein the subject is a human.

20. The method of claim 14, wherein the one or more polypeptides are administered orally or intravenously.

21. The method of claim 14, wherein the one or more polypeptides have been subject to fermentation.

22. The method of claim 14, wherein the one or more polypeptides are at least about 85%, 90% or 95% purified, separated or isolated from or free of non-proteinaceous components of FWGE.

23. A method of reducing and/or inhibiting the growth and/or proliferation of a cancer cell, the method comprising contacting the cancer cell with fermented wheat germ extract polypeptides (FWGP), wherein the cancer is selected from the group consisting of lymphoma, lung cancer, breast cancer, colon cancer, and hepatic cancer, wherein the FWGP is at least about 90% purified, separated or isolated from non-proteinaceous components of FWGE.

24. The method of claim 23, wherein the FWGP is at least about 95% or 99% purified, separated or isolated from non-proteinaceous components of FWGE.

25. The method of claim 23, wherein the FWGP has been subject to fermentation.

26. The method of claim 23, further comprising contacting the cancer cell with one or more wheat polypeptides selected from the group consisting of early-methionine-labelled polypeptide, late embryogenesis abundant protein, FGAS022985 (*Triticum aestivum* FGAS: Library 6 CAP GATE 1), thioredoxin h, Em protein H2, translational inhibitor protein (*Triticum aestivum* FGAS: Library 4 Gate 8), FGAS051302 (*Triticum aestivum* FGAS: TaLt7), dimeric alpha-amylase inhibitor, G468.105F06R010929 G468 (*Triticum aestivum* cDNA clone G468105F06), wsi18 protein induced by water stress, reversibly glycosylated polypeptide, FGAS014876 (*Triticum aestivum* FGAS: Library 4 Gate 8), cold shock protein-1, FGAS021443 (*Triticum aestivum* FGAS: Library 5 GATE 7), subunit CM3 of alpha-amylase tetrameric inhibitor (hageman factor inhibitor), FGAS030061 (*Triticum aestivum* FGAS: Library 6 CAP GATE 1), protein disulfide isomerase, wheat germ agglutinin isolectin D, wheat germ agglutinin isolectin A, n-acetyl-neuraminyllactose-wheat germ agglutinin isolectin complexes, FGAS029900 (*Triticum aestivum* FGAS: Library 6 CAP GATE 1), FGAS021317 (*Triticum aestivum* FGAS: Library 5 GATE 7), desiccation-related protein pcc13-62, BRY_901 BRY (*Triticum aestivum* cDNA clone P10-1L), high molecular weight glutenin subunit, FGAS014507 (*Triticum aestivum* FGAS: Library 4 Gate 8), group 3 late embryogenesis abundant protein, serpin, FGAS045291 (*Triticum aestivum* FGAS: TaLt6), carboxymethylenebutenolidase, carboxymethylenebutenolidase-like protein, FGAS075594 (*Triticum aestivum* FGAS: Library 2 Gate 3), G608.105K18F010906 G608 (*Triticum aestivum* cDNA clone G608105K18), ABA-inducible protein WRAB1, WHE2989_H12_P23ZS Wheat dormant embryo (*Triticum aestivum* cDNA clone WHE2989_H12_P23, *Triticum aestivum* LEA1 protein (LEA1), *Triticum aestivum* LEA2 protein (LEA2), *Triticum aestivum* LEA3 protein (LEA3), FGAS017876 (*Triticum aestivum* FGAS: Library 5 GATE 7), pathogenesis-related protein 5, and d-ribulose-5-phosphate 3-epimerase secreted protein.

27. The method of claim 23, further comprising contacting the cancer cell with a chemotherapeutic agent and/or an antibody against a tumor associated antigen.

28. The method of claim 23, wherein the cancer cell is in vivo.

29. The method of claim 23, wherein the cancer cell is in vitro.

30. The method of claim 23, wherein the cancer is a lymphoma.

31. The method of claim 23, wherein the cancer is a lung cancer.

32. The method of claim 23, wherein the FWGP is free of non-proteinaceous components of FWGE.

33. A method of reducing and/or inhibiting the growth and/or proliferation of a cancer cell in a subject, the method comprising administering to the subject an effective amount of fermented wheat germ extract polypeptides (FWGP), wherein the cancer is selected from the group consisting of lymphoma, lung cancer, breast cancer, colon cancer, and hepatic cancer, wherein the FWGP is at least about 90% purified, separated or isolated from non-proteinaceous components of FWGE.

34. The method of claim 33, wherein the FWGP is at least about 95% or 99% purified, separated or isolated from non-proteinaceous components of FWGE.

35. The method of claim 33, wherein the cancer is a lymphoma.

36. The method of claim 33, wherein the cancer is a lung cancer.

37. The method of claim 33, further comprising co-administering the one or more polypeptides with a chemotherapeutic agent and/or an antibody against a tumor associated antigen.

38. The method of claim 33, wherein the FWGP has been subject to fermentation.

39. The method of claim 33, wherein the FWGP comprises one or more wheat polypeptides selected from the group consisting of early-methionine-labelled polypeptide, late embryogenesis abundant protein, FGAS022985 (*Triticum aestivum* FGAS: Library 6 CAP GATE 1), thioredoxin h, Em protein H2, translational inhibitor protein (*Triticum aestivum* FGAS: Library 4 Gate 8), FGAS051302 (*Triticum aestivum* FGAS: TaLt7), dimeric alpha-amylase inhibitor, G468.105F06R010929 G468 (*Triticum aestivum* cDNA clone G468105F06), wsi 18 protein induced by water stress, reversibly glycosylated polypeptide, FGAS014876 (*Triticum aestivum* FGAS: Library 4 Gate 8), cold shock protein-1, FGAS021443 (*Triticum aestivum* FGAS: Library 5 GATE 7), subunit CM3 of alpha-amylase tetrameric inhibitor (hageman factor inhibitor), FGAS030061 (*Triticum aestivum* FGAS: Library 6 CAP GATE 1), protein disulfide isomerase, wheat germ agglutinin isolectin D, wheat germ Agglutinin isolectin A, n-acetylneuraminyllactose-wheat germ agglutinin isolectin complexes, FGAS029900 (*Triticum aestivum* FGAS: Library 6 CAP GATE 1), FGAS021317 (*Triticum aestivum* FGAS: Library_5 GATE 7), desiccation-related protein pcc13-62, BRY 901 BRY (*Triticum aestivum* cDNA clone P 10-1L), high molecular weight glutenin subunit, FGAS014507 (*Triticum aestivum* FGAS: Library 4 Gate 8), group 3 late embryogenesis abundant protein, serpin, FGAS045291 (*Triticum aestivum* FGAS: TaLt6), carboxymethylenebutenolidase, carboxymethylenebutenolidase-like protein, FGAS075594 (*Triticum aestivum* FGAS: Library 2 Gate 3), G608.105K 18F010906 G608 (*Triticum aestivum* cDNA clone G608105K 18), ABA-inducible protein WRAB 1, WHE2989 H12 P23ZS Wheat dormant embryo (*Triticum aestivum* cDNA clone WHE2989_H12_P23, *Triticum Aestivum* LEA1 protein (LEA1), *Triticum aestivum* LEA2 protein (LEA2), *Triticum aestivum* LEA3 Protein (LEA3), FGAS017876 (*Triticum aestivum* FGAS: Library 5 GATE 7), pathogenesis-related protein 5, and d-ribulose-5-phosphate 3-epimerase secreted protein.

40. The method of claim 33, wherein the subject is a human.

41. The method of claim 33, wherein the FWGP is administered orally or intravenously.

42. The method of claim 33, wherein the FWGP is free of non-proteinaceous components of FWGE.

* * * * *